United States Patent
Krauss et al.

(10) Patent No.: US 8,920,766 B2
(45) Date of Patent: Dec. 30, 2014

(54) QUANTUM NANOSTRUCTURES, COMPOSITIONS THEREOF, AND METHODS OF MAKING AND USING SAME

(71) Applicant: University of Rochester, Rochester, NY (US)

(72) Inventors: Todd D. Krauss, Pittsford, NY (US); Christopher M. Evans, Chicago, IL (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/972,485

(22) Filed: Aug. 21, 2013

(65) Prior Publication Data

US 2014/0170692 A1    Jun. 19, 2014

Related U.S. Application Data

(60) Provisional application No. 61/691,489, filed on Aug. 21, 2012.

(51) Int. Cl.

| | |
|---|---|
| *B82Y 40/00* | (2011.01) |
| *C01B 17/20* | (2006.01) |
| *C01B 19/00* | (2006.01) |
| *C01B 19/04* | (2006.01) |
| *C01G 11/00* | (2006.01) |
| *C01G 11/02* | (2006.01) |
| *G01N 21/64* | (2006.01) |

(52) U.S. Cl.
CPC ........... *G01N 21/6486* (2013.01); *Y10S 977/70* (2013.01); *Y10S 977/773* (2013.01); *Y10S 977/774* (2013.01); *Y10S 977/775* (2013.01); *Y10S 977/813* (2013.01); *Y10S 977/824* (2013.01); *Y10S 977/825* (2013.01); *Y10S 977/927* (2013.01)
USPC ........ 423/508; 423/509; 423/511; 423/561.1; 423/566.1; 977/700; 977/773; 977/774; 977/775; 977/813; 977/824; 977/825; 977/927

(58) Field of Classification Search
CPC ........ B82Y 40/00; C01B 17/20; C01B 19/00; C01B 19/007; C01B 19/04; C01G 11/00; C01G 11/02
USPC .................. 423/508, 509, 511, 561.1, 566.1; 977/700, 773, 774, 775, 813, 824, 825, 977/927
See application file for complete search history.

(56) References Cited

U.S. PATENT DOCUMENTS

| | | | |
|---|---|---|---|
| 7,208,133 B2 * | 4/2007 | Cho et al. | 423/508 |
| 7,833,506 B2 * | 11/2010 | Rauscher et al. | 423/509 |
| 2011/0070147 A1 * | 3/2011 | O'Brien et al. | 423/509 |

* cited by examiner

Primary Examiner — Timothy Vanoy
(74) Attorney, Agent, or Firm — Hodgson Russ LLP

(57) ABSTRACT

Provided are methods for making quantum nanostructures based on use of a combination of nucleation and growth precursors. The methods can be used to provide quantum nanostructures of a selected size. Also provided are quantum nanostructures, compositions comprising the quantum nanostructures, and uses of the quantum nanostructures. The quantum nanostructures can be used, for example, in imaging applications.

15 Claims, 17 Drawing Sheets
(9 of 17 Drawing Sheet(s) Filed in Color)

Table 1

|  | C% | O% | Cd% | S% | CdS ratio | CdS corrected | D (nm) | $Cd_2/Cd_1$ ratio | $S_2/S_1$ ratio | Surface % Cd | S |
|---|---|---|---|---|---|---|---|---|---|---|---|
| CdS - A | 75.36 | 12.73 | 3.95 | 2.78 | 1.42 | 1.36 | 2.84 | 0.45 | 0.50 | 56 | 44 |
| CdS - B | 65.44 | 10.86 | 9.76 | 3.54 | 0.94 | 0.92 | 3.96 | 0.08 | 0.84 | 13 | 87 |
| CdS - C | 61.71 | 19.32 | 2.92 | 1.19 | 2.44 | 2.38 | 4.26 | 0.94 | 0.12 | 91 | 9 |

Table 2

|  |  |  | Binding Energy (eV) | Area | FWHM (eV) |
|---|---|---|---|---|---|
| CdS - A | Cd 3d 3/2 | peak 1 | 412.20 | 2045 | 1.45 |
|  |  | peak 2 | 413.10 | 901 | 1.65 |
|  | Cd 3d 5/2 | peak 1 | 405.40 | 2999 | 1.45 |
|  |  | peak 2 | 406.30 | 1358 | 1.65 |
|  | S 2p 1/2 | peak 1 | 163.15 | 83 | 1.56 |
|  |  | peak 2 | 164.00 | 43 | 1.57 |
|  | S 2p 3/2 | peak 1 | 161.95 | 164 | 1.56 |
|  |  | peak 2 | 163.00 | 88 | 1.57 |
| CdS - B | Cd 3d 3/2 | peak 1 | 411.91 | 6913 | 1.41 |
|  |  | peak 2 | 413.12 | 536 | 1.42 |
|  | Cd 3d 5/2 | peak 1 | 405.16 | 10012 | 1.41 |
|  |  | peak 2 | 406.32 | 804 | 1.42 |
|  | S 2p 1/2 | peak 1 | 162.60 | 229 | 1.26 |
|  |  | peak 2 | 163.43 | 193 | 1.30 |
|  | S 2p 3/2 | peak 1 | 161.40 | 454 | 1.25 |
|  |  | peak 2 | 162.20 | 383 | 1.29 |
| CdS - C | Cd 3d 3/2 | peak 1 | 412.00 | 1061 | 1.70 |
|  |  | peak 2 | 413.30 | 543 | 1.69 |
|  |  | peak 3 | 414.80 | 388 | 1.81 |
|  | Cd 3d 5/2 | peak 1 | 405.20 | 1571 | 1.69 |
|  |  | peak 2 | 406.50 | 816 | 1.68 |
|  |  | peak 3 | 408.00 | 555 | 1.82 |
|  | S 2p 1/2 | peak 1 | 163.07 | 52 | 1.81 |
|  |  | peak 2 | 164.00 | 6 | 1.88 |
|  | S 2p 3/2 | peak 1 | 161.86 | 102 | 1.80 |
|  |  | peak 2 | 162.77 | 12 | 1.90 |

Figure 12

QUANTUM NANOSTRUCTURES, COMPOSITIONS THEREOF, AND METHODS OF MAKING AND USING SAME

STATEMENT REGARDING FEDERALLY SPONSORED RESEARCH

This invention was made with government support under contract no. CHE-1012681 awarded by the National Science Foundation. The government has certain rights in the invention.

FIELD OF THE DISCLOSURE

This disclosure generally relates to quantum nanostructures (e.g., quantum dots) and methods of making and using same. More particularly, the disclosure relates to methods of making quantum nanostructures using reactants having different reactivity.

BACKGROUND OF THE DISCLOSURE

Quantum dots (QDs) and other quantum nanoparticles have been prepared and their properties have been documented and described. One proposed use of quantum dots is in the field of biochemistry wherein these particles provide photoluminescent markers for whole cells. In addition, they can be used as markers that allow one to track the activity of individual cellular ligands, for example, organelles or macromolecules.

The essential components in the synthesis of II-VI and IV-VI QDs have remained largely unchanged for 20 years, typically employing tertiary phosphine chalcogenides and metal salts as the reactive precursors. Notable advances include removing the need for pyrophoric compounds and designing ligands to obtain a greater control over QD size, size distribution, and shape. However, the synthetic conversion yield can be very low (<2%) for normal reactions. Also, inconsistencies can arise from the fact that traditional QD syntheses are based on tertiary phosphine chalcogenide molecular precursors, which at temperatures under 200° C. are largely unreactive and thus not responsible for QD formation.

Most current methodologies for the production of II-VI and IV-VI colloidal semiconductor quantum dots (QDs) rely upon the slow addition precursor to nucleated particles for the growth of larger structures. QDs grow larger with time so a reaction must be quenched at a precise time to achieve a desired nanoparticle size. This can be laborious and inexact which is a major source of batch-to-batch inconsistencies and contributes to the very high price (>$100,000 per gram) for commercial sources of quantum dots.

BRIEF SUMMARY OF THE DISCLOSURE

In an aspect, the present disclosure provides methods (also referred to herein as processes) for making colloidal quantum nanomaterials (QNs). Quantum nanostructures as used herein includes, but is not limited to, nanocrystals, quantum dots, magic size clusters (MSCs), quantum rods, quantum wires, dendridic inorganic nanostructures, tetrapods, cubes, core-shell and alloy structures of the preceding, and the like. Quantum dots that can be prepared by the present methods include, but are not limited to, cores, core-shells, alloyed cores, and alloyed core-shells, and the like.

The methods are based on the reaction between cation source(s) and anion source(s). The methods are based on the surprising result that the ability of a cation-anion chemical precursor pair to make a QN monomer is governed by, for example, the acid-base equilibria associated with cation source and anion source. The methods of the present invention can provide size control through, for example, (1) use of reactive precursors with selected reactivity that can react with QDs already growing but not nucleate new QDs, and (2) use of reaction temperatures at which Oswald ripening, which can result in a loss of size control, is diminished or precluded.

In an embodiment, the method comprises the steps of: (a) providing a first cation source and a second cation source, each cation source comprising a metal and at least one ligand, or a first anion source and a second anion source, each anion source comprising a metal and at least one ligand; (b) if the cation sources are used, providing an anion source comprising a metal and at least one ligand, or if the anion sources are used, providing a cation source comprising a metal and at least one ligand; (c) contacting (a) and (b), optionally, in a solvent, to form a reaction mixture; and (d) maintaining (c) at a temperature and time sufficient to form the quantum nanostructures. The first cation or anion source has substantially greater reactivity than the second anion or cation source, respectively. Optionally, the method further comprises the step of providing of one or more additional cation sources and/or one or more additional anion sources, and contacting the additional sources with (a) and (b), optionally, in a solvent, to form the reaction mixture.

In an embodiment, the method comprises the steps of: (a) contacting a first cation source and a second cation source, the first cation source comprising a metal and at least one first ligand and the second cation source comprising the metal and at least one second ligand, and an anion source comprising a metal and at least one ligand, optionally, in a solvent, to form a reaction mixture; and (b) maintaining the reaction mixture from (a) at a temperature and time sufficient to form the quantum nanostructures, where the first cation source is a nucleation source and the second cation source is a growth source, and at least 90% of the first cation source reacts before more than 10% of the second cation source reacts.

In an embodiment, the method for preparing quantum nanostructures comprises the steps of: (a) contacting a first cation source comprising a metal and at least one first ligand, where the first cation source is a nucleation source, and an anion source comprising a metal and at least one ligand, optionally, in a solvent, to form a reaction mixture; (b) maintaining the reaction mixture from (a) at a temperature and time sufficient to form quantum nanostructure nucleates and such that the quantum nanostructure nucleate size stabilizes; (c) adding a second cation source comprising the metal and at least one second ligand to the reaction mixture from (b), wherein the second source is a growth source; and (d) maintaining the reaction mixture from (c) at a temperature and time sufficient to form the quantum nanostructures.

The methods can provide QNs having a desirable size distribution without the need for any work-up (e.g., washing, precipitation, dialysis, chromatography, and centrifugation) or performing post-preparation procedures to eliminate certain QDs. Accordingly, in an embodiment, the method does not comprise any such work-up or post-preparation procedures.

In an aspect, the present disclosure provides quantum nanostructures and compositions comprising quantum nanostructures. The QNs can have a narrow size distribution. In an embodiment, a plurality of QDs having a narrow size distribution (e.g., the QNs are substantially monodisperse) is provided without work-up (e.g., washing or centrifugation) or performing post-preparation procedures to eliminate certain QDs. In an embodiment, the QNs are substantially monodisperse. The QNs can be used in, for example, thin-film light emitting devices (LEDs), low-threshold lasers, optical amplifier media for telecommunication networks, for relay of encrypted information.

The surface of the QNs can be controlled. A desired surface composition (e.g., surface concentration of anions or cations) can be obtained without the need for post particle formation reactions. For example, the QN can have an anion (e.g., chalcogen) terminated surface, a cation (e.g., Pb or Cd) terminated surface, or a selected combination thereof.

In an aspect, the present disclosure provides biological conjugates comprising the QNs. In an embodiment, the biological conjugates comprise QNs and a biological analyte conjugated thereto.

In an aspect, the disclosure relates to methods of using the QNs. The QNs can be used in, for example, imaging methods and transmission of encrypted information.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 12. Table 2—Example of detailed XPS peak analysis data. Raw XPS data was fit with Gaussian functions as shown in FIG. 6. In each sample, peak 1 indicates signals from inner atoms of Cd or S (also represents the blue lines (fitting curves) in FIG. 2), while peak 2 represents contributions to signals from surface atoms (the green lines (fitting curves)). Peak 3 in the CdS-C sample shows the signals from oxidized cadmium on the surface of QDs.

when the surface of the QDs was ~30% covered by Cd. The QY then decreased to 2% after more Cd precursor was added. The decrease of QY for additional Cd addition is attributed to oxidation since under normal synthesis conditions the PL intensity was observed to be completely recovered after an injection of one complete Cd monolayer.

Figure 15:
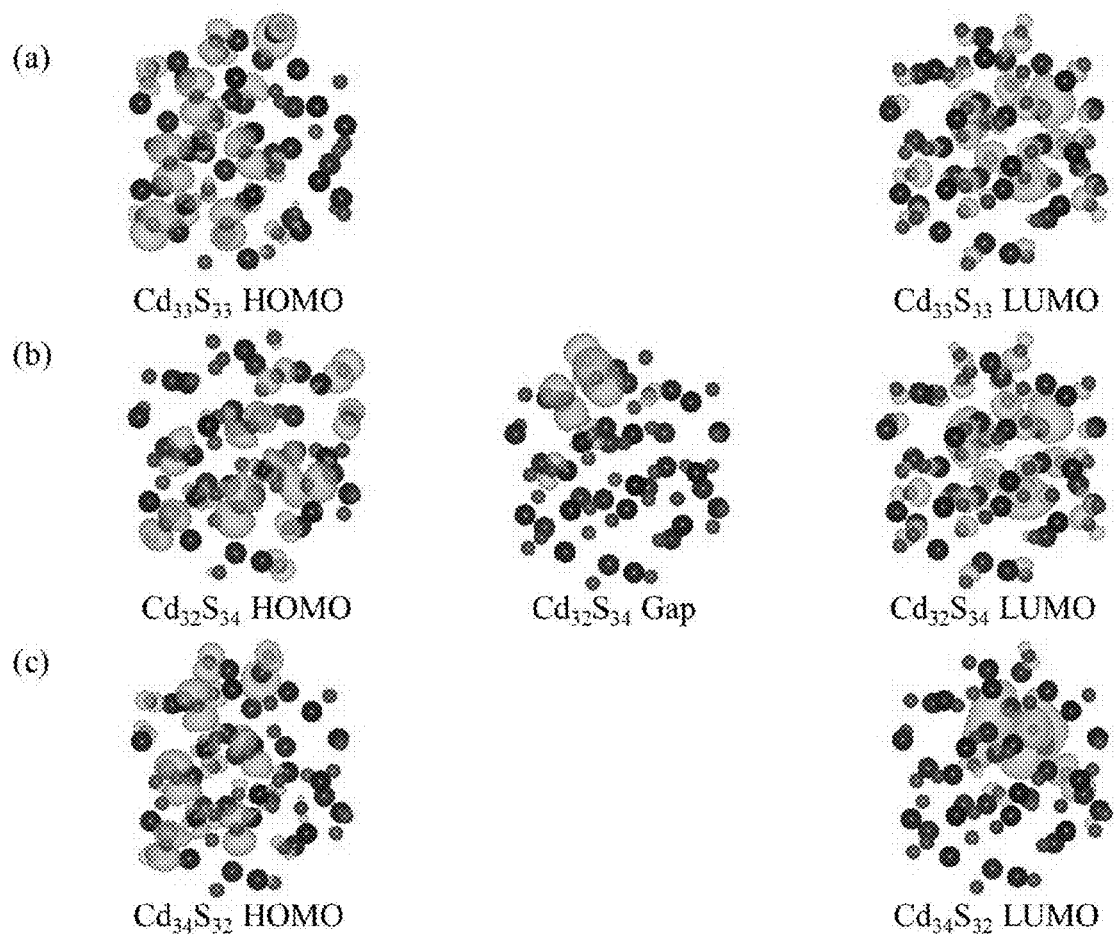

FIG. 15. Exemplary charge densities of the highest occupied and lowest unoccupied molecular orbitals (HOMO and LUMO) and mid-gap states in (a) ideal stoichiometric CdS (b) S-rich QD and (c) Cd-rich QD. The HOMO and LUMO of each system look similar and are delocalized over most of the QD. The mid-gap state introduced in the S-rich cluster is strongly localized in the S-rich region.

Figure 16:
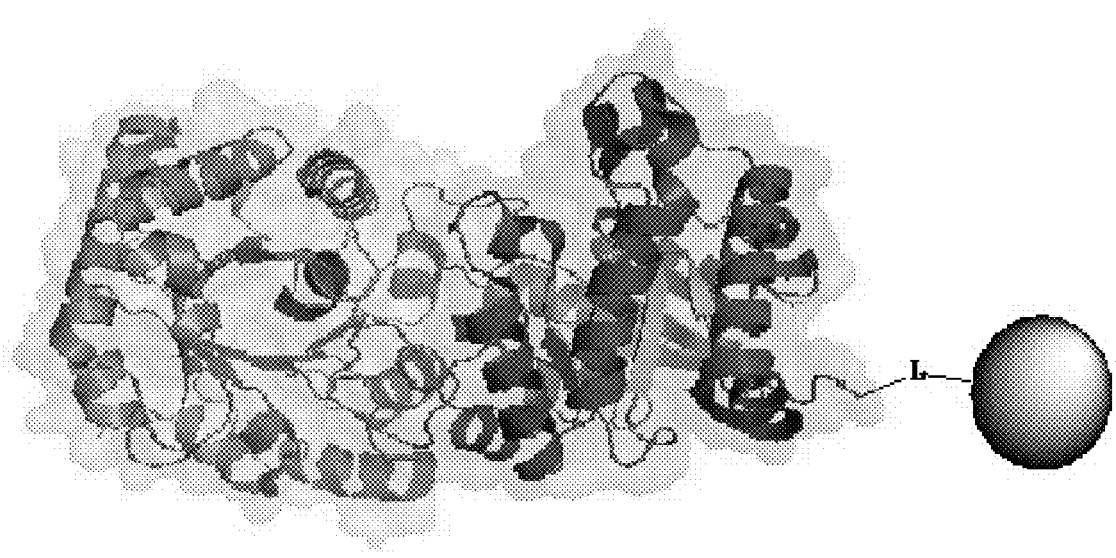

FIG. 16. Graphical representation of an enzyme attached to a disclosed nanoparticle by way of a linking group (L).

Figure 17:
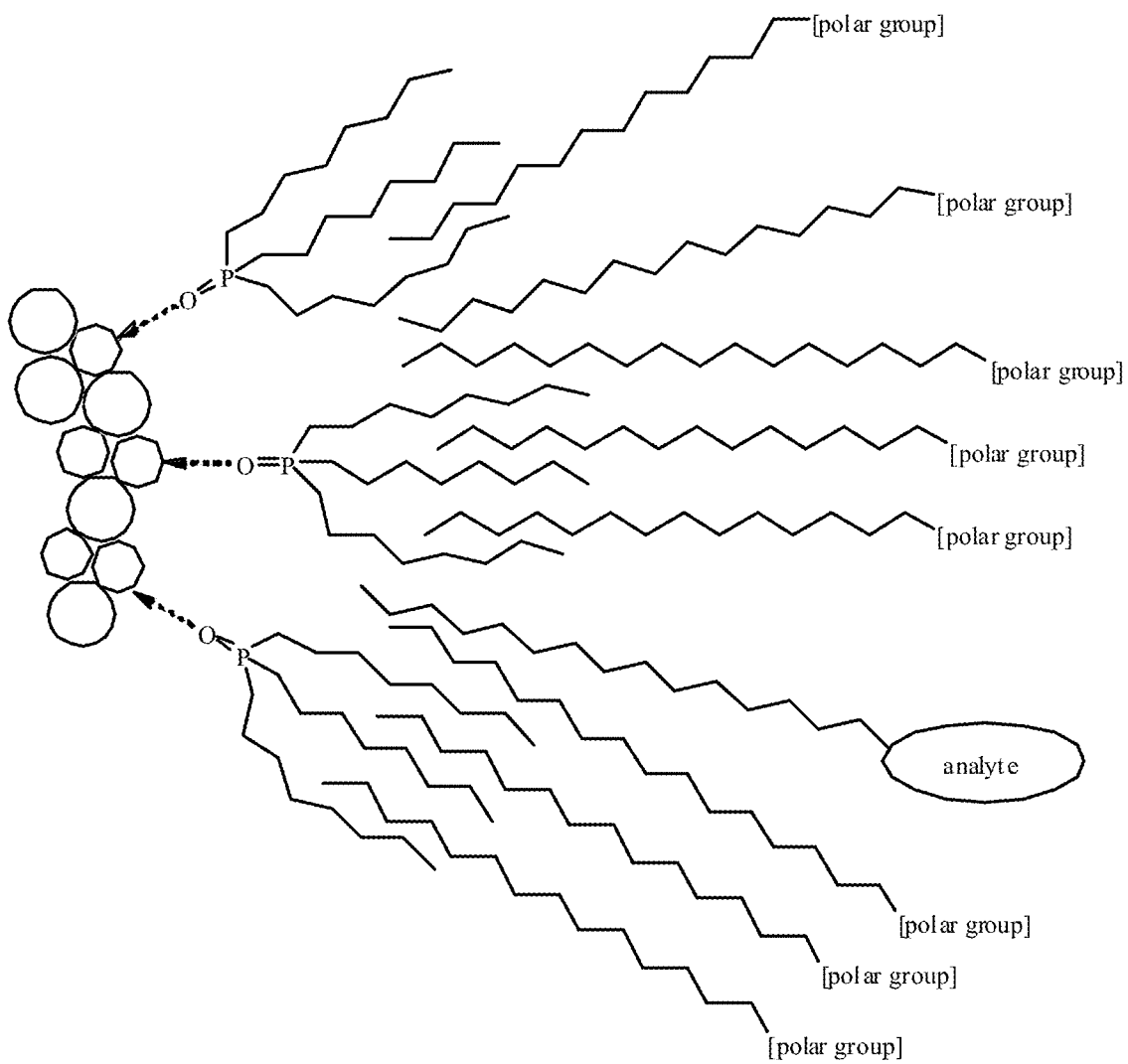

FIG. 17. Graphical representation of conjugation of a biological analyte to the passivation layer of a continuously photoluminescent nanoparticle using a lipid bilayer approach.

Figure 18:
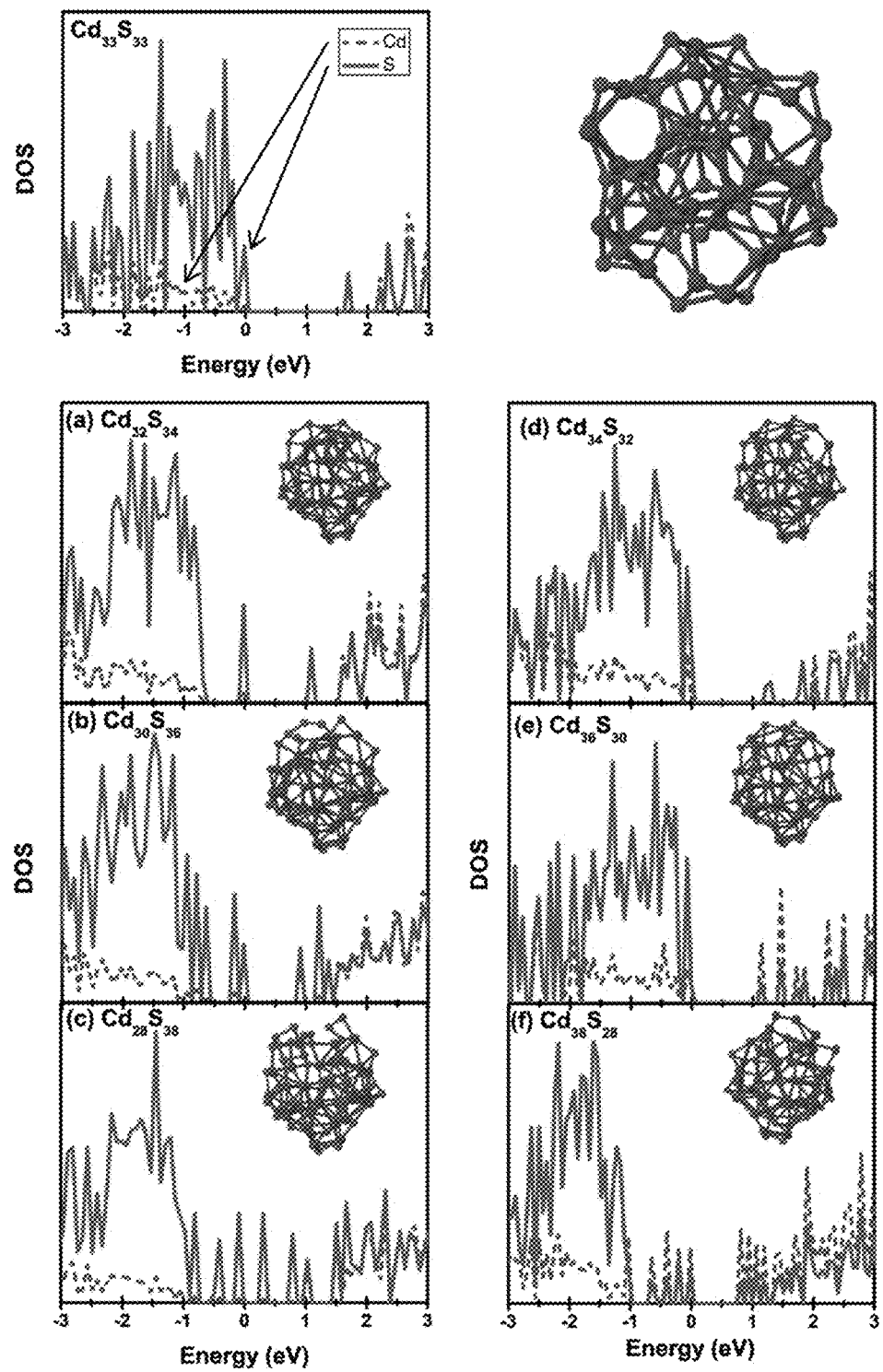

FIG. 18. (Top Panel) Densities of Cd (blue) and S (red) states and geometry for a stoichiometric CdS QD. Panels (a-c) and (d-f) show the densities of states for increasingly S and Cd-rich systems, respectively. In the S rich systems, a series of mid-gap states emerges and completely fills the band gap. The zero of energy is set equal to the energy of the highest occupied orbital.

Figure 19:
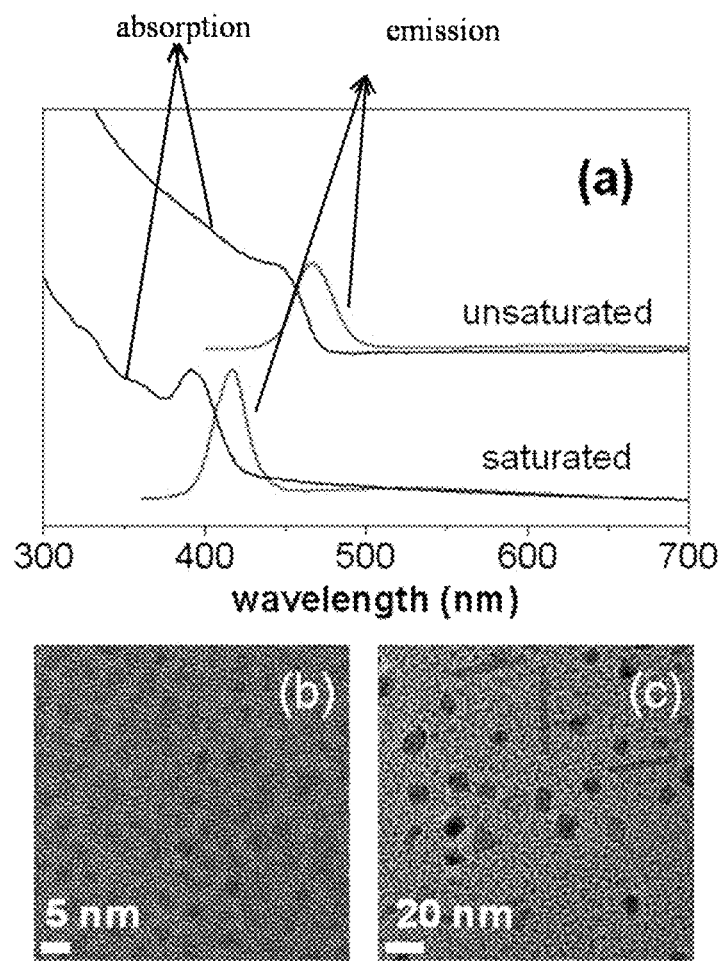

FIG. 19. (a) Absorption and emission spectra of CdS QDs synthesized in saturated (tetradecane) and unsaturated (1-octadecene) solvent. TEM images of the resulting CdS QD product resulting from synthesis in saturated (panel b) and unsaturated (panel c) solvent.

Figure 20:
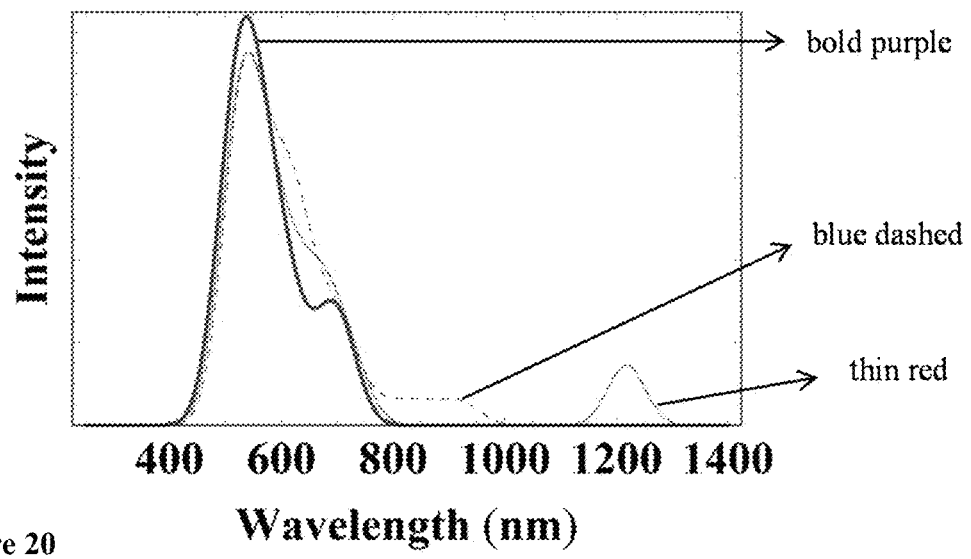

FIG. 20. Calculated absorption spectra of stoichiometric (bold purple line), Cd-rich (blue dashed line), and S-rich (thin red line) CdS QDs.

DETAILED DESCRIPTION OF THE DISCLOSURE

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Process

In an aspect, the present disclosure provides methods (also referred to herein as processes) for making colloidal quantum nanomaterials (QNs). Quantum nanostructures as used herein includes, but are not limited to, nanocrystals, quantum dots, magic size clusters (MSCs) quantum rods, quantum wires, dendridic inorganic nanostructures, tetrapods, cubes, core-shell and alloy structures of the preceding, and the like. Quantum nanostructures include any 3-D geometry whereby one or more dimensions is of such size to be considered quantum confined. For semiconductors, quantum confinement is based upon the inherent exciton Bohr radii of the constituent atoms. Quantum dots that can be prepared by the present methods include, but are not limited to, cores, core-shells, alloyed cores, and alloyed core-shells, and the like. Any quantum nanostructure structure which is produced using an organo-phosphine-chalcogenide compound (e.g. TOP-Se) can be formed using the methods disclosed herein.

The methods are based on the reaction between cation source(s) and anion source(s). The methods are based on the surprising result that the ability of a cation-anion chemical precursor pair to make a QN monomer is governed by, for example, the acid-base equilibria associated with cation source and anion source. The QN monomers react to form QNs. Without intending to be bound by any particular theory, it is considered that the reaction forming the QNs is controlled by the amount of reactants and, therefore, QNs having a desired size and/or composition can be achieved by rational selection of the acid-base reactants.

The methods of the present invention provide advantages over previously known methods such as, for example, the higher reactivity means that nearly all or all precursor is consumed and the yield can approach 100% and the lack of left over excess precursor can obviates the need for purification of the QDs by centrifugation, which can reduce the time to make the QDs by an order of magnitude or more.

The methods of the present invention can provide size control through, for example, (1) use of reactive precursors with selected reactivity that can react with QDs already growing but not nucleate new QDs, and (2) use of reaction temperatures at which Oswald ripening, which can result in a loss of size control, is diminished or precluded. In an embodiment, the method does not comprise a step of quenching the reaction.

The QN monomers are formed by reaction between a cation source and an anion source. The present methods use at least two cation sources or at least two anion sources where the reactivity of one of the sources (a first source/the nucleation source) is substantially greater than the reactivity of a second source (a second source/growth source). Selecting the relative amounts and/or relative reactivity (e.g., relative pKa) of the nucleation cation/anion source and growth cation/anion source results in formation of quantum nanomaterials with improved yields and size distributions compared to known methods.

In the method, a reaction mixture is formed that comprises the at least two cation sources or at least two anion sources. In various embodiments, the two cation sources or two anion sources comprise the same metal or different metals. In an embodiment, the two cation sources or two anions sources comprise at least one different ligand. The reaction mixture also comprises, if two cation sources are used, at least one anion source, or, if two anion sources are used, at least one cation source. The reaction can comprise additional cation sources and/or anion sources.

In an embodiment, the method comprises the steps of: (a) providing a first cation source and a second cation source, each cation source comprising a metal and at least one ligand, or a first anion source and a second anion source, each anion source comprising a metal and at least one ligand; (b) if the cation sources are used, providing an anion source comprising a metal and at least one ligand, or if the anion sources are used, providing a cation source comprising a metal and at least one ligand; (c) contacting (a) and (b), optionally, in a solvent, to form a reaction mixture; and (d) maintaining (c) at a temperature and time sufficient to form the quantum nanostructures. The first cation or anion source has substantially greater reactivity than the second anion or cation source, respectively. Optionally, the method further comprises the step of providing of one or more additional cation sources and/or one or more additional anion sources, and contacting the additional sources with (a) and (b), optionally, in a solvent, to form the reaction mixture.

In another embodiment, the method comprises the steps of: (a) contacting a first cation source and a second cation source, each cation source comprising a metal and at least one ligand, wherein the first cation source is a nucleation source and the second cation source is a growth source, and an anion source comprising a metal and at least one ligand, optionally, in a solvent, to form a reaction mixture; and (b) maintaining the reaction mixture from (a) at a temperature and time sufficient to form the quantum nanostructures, where at least 90% of the first cation source reacts before more than 10% of the second cation source reacts.

Optionally, only two cation sources or two anion sources and a cation source (if two anion sources are used) or anion source (if two cation sources are used) are used. In an embodiment, the reaction mixture consists essentially of two cation sources or two anion sources, a cation source (if two anion sources are used) or anion source (if two cation sources are used), and, optionally, a solvent. In another embodiment, the reaction mixture consists of the two cation sources or two anion sources, a cation source (if two anion sources are used) or anion source (if two cation sources are used), and, optionally, a solvent. In an embodiment, only nucleation source(s) are used.

The reaction mixture can be formed in a variety of ways. In an embodiment, all of the sources are combined and, subsequently, the reaction mixture heated to the temperature at which the reaction is carried out. In another embodiment, the cation or anion nucleation source and, if a cation nucleation source is used, the anion source or, if an anion nucleation source is used, the cation source are combined and allowed to react for a selected time and, subsequently, the cation or anion growth source added.

In an embodiment, a nucleation source is added first (i.e., the reaction mixture comprises a nucleation source and does not comprise a growth source). For example, the reaction mixture first comprises a cation/anion nucleation source and, if a cation nucleation source is used an anion source and if an anion nucleation source is used a cation source. The reaction is allowed to proceed until the nucleation source is not detectible and/or the QN particle size (which can be referred to as quantum nanostructure nucleates) stabilizes. By "stabilizes" it is meant that the average QN particle sized does not change over a period of from 1 to 600 minutes, including all integer numbers of minutes and ranges therebetween. After the nucleation source is not detectible and/or the QN particle size stabilizes, the growth source is added to the reaction mixture. In another embodiment, the nucleation source and growth source are present in the reaction mixture at the same time (e.g., both sources are added at the same time).

In an embodiment, the method for preparing quantum nanostructures comprises the steps of: (a) contacting a first cation source comprising a metal and at least one ligand, where the first cation source is a nucleation source, and an anion source comprising a metal and at least one ligand, optionally, in a solvent, to form a reaction mixture; (b) maintaining the reaction mixture from (a) at a temperature and time sufficient to form quantum nanostructure nucleates and such that the quantum nanostructure nucleate size stabilizes; (c) adding a second cation source comprising a metal and at least one ligand to the reaction mixture from (b), wherein the second source is a growth source; and (d) maintaining the reaction mixture from (c) at a temperature and time sufficient to form the quantum nano structures.

In an embodiment, a method disclosed herein is used to make a QD core particle. In an embodiment, a method disclosed herein is used to make a QD shell. In an embodiment, a method disclosed herein is used to make both the core and shell of a core-shell QD.

One of the cation/anion sources is a nucleation source and the other cation/anion source is a growth source. The nucleation source has substantially greater reactivity than the growth source. One having skill in the art will appreciate that the reactivity of the sources can vary widely based on the nature, structure, etc. of the individual sources and the temperature at which the reaction is carried out. Thus, the relative reactivity (i.e., difference in reactivity) required to achieve the stated result(s) of the present disclosure is dependent on such factors.

The nucleation source is a fast reacting source. By "fast reacting" it is meant the nucleation source is consumed (e.g., greater than 95% reacted, greater than 99% reacted, or no longer detectible) in less than 1 minute. In an embodiment, the nucleation source is consumed in 0.01 minute to 0.99 minutes, including all values to the 0.01 minute and ranges therebetween. In various embodiments, the nucleation source is consumed in less than 0.9 minutes, less than 0.8 minutes, less than 0.7 minutes, less than 0.6 minutes, less than 0.5 minutes, less than 0.4 minutes, less than 0.3 minutes, less than 0.2 minutes, or less than 0.1 minutes.

The growth source is a slow reacting source. By "slow reacting" it is meant the growth source is consumed (e.g., greater than 95% reacted, greater than 99% reacted, or no longer detectible) in less than 24 hours. In an embodiment, the nucleation source is consumed in 10 minutes to 24 hours, including all integer values to the minute and ranges therebetween. In various embodiments, the growth source is not consumed in less than 7 hours, less than 6 hours, less than 5 hours, less than 4 hours, less than 3 hours, less than 2 hours, less than 1 hour, less than 0.5 hour, or less than 0.25 hour.

Figure 2:
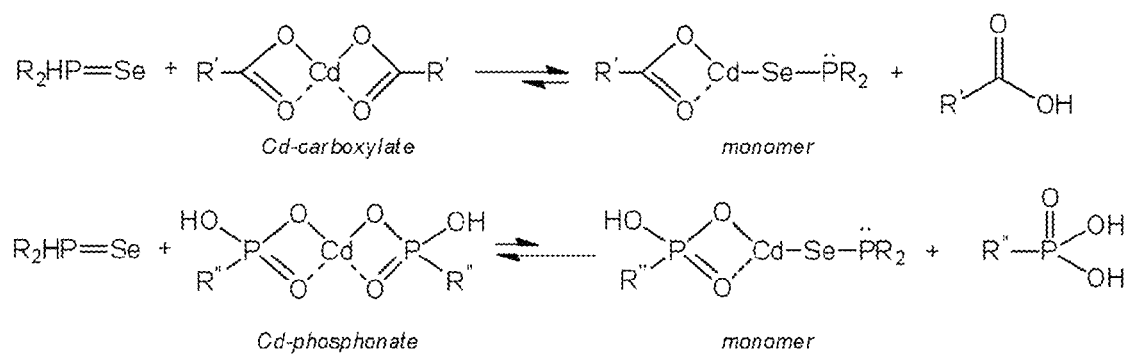
FIG. 2. Scheme 1. An example of acid-base equilibrium kinetics directing monomer formation rate.

The reactivity of the sources can be determined by, for example, the relative acidity/basicity (e.g., the difference in pKa of the nucleation source and growth source) of two or more anion/cation ligands, as shown in FIG. 2 and discussed in Example 2. In an embodiment, the difference in pKa between the nucleation source and growth source is at least 1.5. In various embodiments, the difference is at least 1.6, at least 1.7, at least 1.8, at least 1.9, at least 2.0, at least 2.1, at least 2.2, at least 2.3, at least 2.4, at least 2.5, at least 3.0, at least 3.5, or at least 4.0.

The cation sources have a metal and one or more ligands (e.g., anionic ligands). Examples of cation sources include metal carboxylate complexes (e.g., $Cd(oleate)_2$), metal halides (e.g., $CdCl_2$), metal phosphates (e.g., cadmium phosphates), metal phosphinates (e.g., cadmium phosphinates), metal cyanides (e.g., $Cd(CN)_2$), metal nitrates, (e.g., $Cd(NO_3)_2$), and metal hydroxides(e.g., $Cd(OH)_2$).

The cation source can include any metal or metalloid (e.g., a metal cation or metalloid cation) that forms a stable ligand complex. Examples of suitable metals include, transition metals (e.g., zinc and cadmium), Group 2 metals, Group 3 metals (e.g., gallium and indium), Group 4 metals/metalloids (e.g., silicon, germanium, and lead) and Group 6 metals/metalloids, and mercury.

The ligand can be an acidic ligand. For example, the acidic ligand can be an organic acid (which is present in a deprotonated, anionic form as a ligand bound to a metal). The acid can have hydrophobic groups (e.g., aliphatic groups and/or aromatic groups). For example, the acid has an alkyl group comprising from 1 to 24 carbons, including all integer number of carbons and ranges therebetween.

Examples of suitable organic acids include, carboxylic acids (e.g., acetic acid, propanoic acid, butanoid acid, hexanoic acid, heptanoic acid, octanoic acid, nonanoic acid, decanoic acid, undecanoic acid, dodecanoic acid, tridecanoic acid, tetradecanoic acid, pentadecanoic acid, spalmitoic acid, arachidoate acid, erucate acid, aracidonic acid, pentadecanoic acid, oleic acid, stearic acid, erucic acid, aracidonic acid, linoleic, and linoleinic acid), phosphonic acids, including for example, alkyl phosphonic acids, (e.g., methylphosphonic acid, (aminomethyl)phosphonic acid, methylenediphosphonic acid, vinylphosphonic acid, phosphonoacetic acid, ethylphosphonic acid, 2-aminoethylphosphonic acid, etidronic acid, iminodi(methylphosphonic acid), 3-phosphonicpropionic acid, propylphosphonic acid, 3-aminopropylphosphonic acid, (3-bromopropyl)phosphonic acid, allylphosphonic acid, nirtilotri(methylphosphonic acid), nitrilotris(methylene)triphosphonic acid, N,N-bis(phosphonomethyl)glycine, tert-butylphosphonic acid, N-(phosphonomethyl)imino diacetic acid, N-(2-hydroxyethyl)imiinobis (methylphosphonic acid), N-(phosphonomethyl) iminodiacetic acid, 6-phosphonohexanoic acid, octylphosphonic acid, 1,8-octane diphosphonic acid, diethylentriaminpentakis(methylphosphonic acid), 1,10-decyldiphosphonic acid, hexamethylenediamine-N,N,N',N'-tetrakis(methylphosphonic acid), and hexadecylphosphonic acid) and aryl phosphinic acids (e.g., phenyl phosphonic acid, 4-bromobenzylphosphonic acid, and 4-aminobenzylphonic acid), and phosphinic acids, including for example, alkyl phosphinic acids (e g, dimethylphosphinic acid, diisooctylthiophosphinic acid, diisooctylphosphinic acid, diisooctyldithiophosphinic acid) and aryl phosphinic acids (e.g., phenylphosphinic acid, diphenylphosphinic acid, bis(4-methoxyphenyl)phosphinic acid).

Examples of suitable cation sources include lead acetate, lead oleate, lead propanoate, lead butanoate, lead pentanoate, lead hexanoate, lead heptanoate, lead octanoate, lead nonanoate, lead decanoate, lead undecanoate, lead dodecanoate, lead tridecanoate, lead tetradecanoate, lead pentadecanoate, lead spalmitoate, lead arachidoate, lead stearate, lead erucate, lead aracidonate, lead linooleate, and lead linoleinate. Additional examples include cadium analogs and zinc analogs of the lead compounds in the preceeding example. Additional examples of cation sources include, halides such as $GaCl_3$ and $InCl_3$ and single source precursors such as $Ga(P^tBu_2)_3$.

Examples of nucleation cation/growth cation pairs include cadmium carboxylate and cadmium phosphonate, cadmium carboxylate and cadmium phosphinate, lead carboxylate and lead phosphonate, lead carboxylate and lead phosphinate.

The anion sources have a metal or non-metal and one or more ligands. The ligands can be hydrophobic (e.g., having aliphatic groups and/or aromatic groups). It is preferable the ligand have one or more acidic protons (e.g., secondary or primary phosphines/phosphites and secondary or primary arsines). The one or more acidic protons can be donated to a ligand of the cationic source. The anion source can include any metal, non-metal, or metalloid (e.g., metal anion, non-metal anion, or metalloid anion) that forms a stable complex. Examples of suitable non-metals anions include, sulfur (e.g., $S^{2-}$), selenium (e.g., $Se^{2-}$) and phosphorus (e.g., $P^{3-}$). An example of a metalloid anion is tellurium ($Te^{2-}$).

Secondary phosphines useful in the present methods have the general formula R(R')PH. The R and R' groups can independently be n-alkyl and isomers thereof (e.g. iso-butyl, sec-butyl, tert-butyl), and aryl or alkyl groups. Secondary phosphites of the general formula ((R"O)(R"'O)PH) can also be used. The R" and R"' groups can independently be n-alkyl and isomers thereof (e.g., iso-butyl, sec-butyl, tert-butyl), and aryl or alkyl groups.

Examples of secondary monophosphine compounds include, bis(3,5-bis(trimethylsilyl)phenyl)phosphine, bis(4-chlorophenyl)phosphine, bis(3,5-di-tert-butylphenyl)phosphine, bis(3,5-ditrifluoromethylphenyl)phosphine, bis(2-furyl)phosphine, bis(4-methylphenyl)phosphine, 1,2-bis (phenylphosphino)ethane, 1,3-bis(phenylphosphino) propane, bis(4-trifluoromethylphenyl)phosphine, bis(3,4,5-trimethoxyphenyl)phosphine, bis(2,4,6-trimethylphenyl) phosphine, dibenzylphosphine, di-n-butylphosphine, di-tert-butylphosphine, dicyclohexylphosphine, diisobutylphosphine, diisopropylphosphine, diphenylphosphine, phobane, di-2-norbornylphosphine, diethylphosphine, dicyclopentylphosphine, dicyclohexylphosphine, di-t-butylphosphine, di-n-propylphosphine, di-1-adamantylphosphine, 1,3-bis(isopropylphosphino)propane, bis(3,5-dimethylphenyl)phosphine, di-n-octylphosphine, di-n-hexylphosphine, di-n-heptylphosphine, di-n-propylphosphine.

The secondary phosphines can be reacted with a chalcogen (S, Se, Te) source (e.g. sulfur, selenium, tellurium, or compounds thereof) to form secondary phosphine chalcogenide compounds, such as secondary phosphine selenide, secondary phosphine sulfide, secondary phosphine telluride compounds. These compounds may be air stable. In an embodiment, a secondary phosphine chalcogenide compound selected from the group consisting of secondary phosphine selenide, secondary phosphine sulfide, secondary phosphine telluride, secondary phosphine arsenide, secondary phosphine antimonide and combinations thereof can be reacted with a cation source to form QNs.

The secondary phosphines may form diphosphines, which in turn can also react with the cation sources to form MSCs and quantum nanostructures. Suitable diphosphines have the general formula (RR'P—PR"'R""), were each R (R, R', R"', R"") is independently as defined herein as R or R'. Examples of disphosphine compounds include, but are not limited to, tetraphenylbisphosphine.

In an embodiment, the anion source comprises secondary arsine compounds (R(R')AsH) and secondary antimony compounds (R(R')SbH). Examples of these compounds include the As and Sb analogs to the secondary phosphines discussed above. In another embodiment, the anion source is a nitride.

Examples of suitable ligands for anion sources include diphenylphosphine, dialkyl phosphines (e.g., diethyl, dibutyl, diisopropyl, and dioctyl phosphines). An examples of a suitable anion source is sulfur diphenylphosphine selenide.

The cation and anion sources can be present in a variety of forms. For example, the cation sources can be present as neutral compounds (e.g., neutral (i.e., protonated form) acids) or salts (e.g., metal salts or ammonium salts). The sources can be commercially available or synthesized using known methods.

The cation and/or anion source can be formed in situ in the reaction mixture. For example, a reaction mixture comprising elemental sulfur, selenium, or tellurium and a suitable ligand (e.g., a secondary phosphine) is used.

In an embodiment, a cationic ligand is a chealating ligand that is a conjugate base anion and an anionic ligand has an acidic proton that coordinates to a chalcogenide.

The cation sources and anion sources react to form a QN monomer. The QN monomer then reacts with another QN monomer or QN polymer (reaction product of a plurality of QN monomers. The reaction proceeds (the QNs grow) until the monomer is depleted. Without intending to be bound by any particular theory, it is considered the amount of nucleation source(s) determines the number of nuclei that form small QNs and the amount of growth source(s) determines the eventual size. For example, the ratio of nucleation source(s) to growth source(s) can be from 100:1 to 1:100000000, including all ratios and ranges of ratios therebetween. In an embodiment, the ratio is 100:1 to 1:1000. In general, more growth reactant is required to form larger QNs because the volume increases as a cube of reactant amount.

A cation/anion source can be present over a wide range of concentration(s). The concentration(s) of the sources can be used to control particle size. For example, the concentration of a cation/anion source can in the micromolar to millimolar range.

The cation/anion sources are combined to form a reaction mixture. The reaction mixture can also include a solvent (or mixture of solvents). The reaction mixture can, optionally, include a particle growth, nucleation stabilization system (PGNSS).

The reaction mixture can comprise a solvent. The solvent can be a single solvent or a mixture of solvents. The solvents can be incorporated in the reaction mixture in a variety of manners. For example, one or more of the anion/cation sources can dissolved in a solvent and added to the reaction mixture, the anion/cation sources can be added to a solvent, or a solvent added to a mixture of anion/cation sources.

The solvent can be a non-coordinating solvent. Non-limiting examples of non-coordinating solvents include 1-decene, 1-dodecene, 1-tetradecene, 1-hexadecene, 1-octadecene, 1-icosene, and 1-docosene.

The solvent can be a coordinating solvent. Among the different types of coordinating solvents that can be used are alkylphosphines, alkylphosphine oxides, alkylphosphites, alkylphosphates, alkylamines, alkylphosphonic acids, alkylethers, and the like. Solvents suitable for use in preparing the disclosed ternary cores include solvents chosen from trioctylphosphine, tributylphosphine, tri(dodecyl)-phosphine, trioctylphosphine oxide, dibutyl-phosphite, tributyl phosphite, trioctadecyl phosphite, trilauryl phosphite, tris(tridecyl) phosphite, triisodecyl phosphite, bis(2-ethylhexyl)phosphate, tris(tridecyl) phosphate, hexadecylamine, oleylamine, octadecylamine, bis(2-ethylhexyl)amine, octylamine, dioctylamine, trioctylamine, dodecylamine (laurylamine), didodecylamine, tridodecylamine, dioctadecylamine, trioctadecylamine, phenylphosphonic acid, hexylphosphonic acid, tetradecylphosphonic acid, octylphosphonic acid, octadecylphosphonic acid, propylenediphosphonic acid, phenylphosphonic acid, aminohexylphosphonic acid, dioctylether, dioctyl ether/octyl ether, dodecyl ether, hexadecyl ether, octadecyl ether, and octadecene.

In an embodiment, as a result of the relatively low temperatures used in the present method, common organic solvents can be used in any of the steps of the process. Examples of common solvents include, but are not limited to, pentane, hexane, heptane, cyclohexane, benzene, toluene, xylene, chloroform, methylene chloride, acetonitrile, and dimethylformamide.

The preparation of the QNs can be conducted in the presence of a particle growth, nucleation stabilization system (PGNSS). In an embodiment, the reaction mixture comprises a PGNSS. In an embodiment, the PGNSS comprises an alkyl amine, for example, an alkyl amine chosen from octylamine, nonylamine, decylamine, undecylamine, dodecylamine (laurylamine), tridecylamine, tetradecylamine (myristyl amine), pentadecylamine, hexadecylamine (palmitylamine), septadecylamine, octadecylamine, and the like. In addition, unsaturated amines can be used in this aspect, for example, an amine chosen from $\Delta^2$-dodecenylamine, (Z)-$\Delta^9$-tetradecenylamine, (Z)-$\Delta^9$-hexadecenylamine, (Z)-$\Delta^9$-octadecenylamine (oleylamine), (Z,Z)-$\Delta^{9,12}$-octadecadienylamine (linoleylamine), (Z,Z,Z)-$\Delta^{9,12,15}$-octadecatrienylamine (linolenylamine), (Z)-$\Delta^{11}$-eicosenylamine, (Z,Z,Z)-$\Delta^{5,8,11}$-eicosatrienylamine, and (Z)-$\Delta^{13}$-docosenylamine.

The disclosed process can further comprise an optional step comprising isolating the quantum nanostructures. The QNs can be isolated by a variety of methods known in the art. In an embodiment, the QNs are isolated by filtration. In another embodiment, the QNs are isolated by centrifugation.

The reaction can be carried out over a broad temperature range depending on the anion/cation sources and solvents used. For example, the reaction can be carried out at temperatures from −40° C. to 380° C., including all integer ° C. values and ranges therebetween. In an embodiment, the reaction is carried out at 200° C. to 300° C. In an embodiment, the reaction is carried out at 200° C. to 250° C. In various embodiments, the reaction is carried out at less than 250° C. or less than 200° C. The present method can be performed at lower temperatures because of the increased reactivity of the reactants. These reactions can be run at significantly lower temperature than corresponding reactions using tertiary phosphine based anion sources. For example, both PbSe and PbS MSCs or QDs produced using secondary phosphines growth can occur at reduced temperatures (e.g., less than 0° C.).

The reagents used to form the QNs can be combined in any order. In addition, the reagents can be at the same temperature or at any temperature of less than or equal to about 70° C. For example, the cation source can be at a first temperature and the anion source can be at a second different temperature.

The disclosed process can be carried out without the need of an inert atmosphere. However, in an embodiment the step (c) is conducted in an inert atmosphere of a dry inert gas (e.g., nitrogen or argon).

The QNs may comprise a passification layer or coating. Along the surface of the QN can exist one or more compounds that define the hydrodynamic diameter and which act to influence the ability of the structures to function as either a biological probe or to facilitate entry of the nanoparticle into a cellular structure. This layer is otherwise known as a "passification layer." The passivation layer helps to stabilize the QNs. The QNs can be modified to be hydrophilic by exchange of the original passivation layer with one that provides water solubility or water dispersability. The passification layer can comprise any material that acts to stabilize the nanoparticles or that serves as a point of attachment of one or more biological analytes, biologically active substrates, or biologically compatible agents. Non-limiting example include $C_1$-$C_{22}$ carboxylic acids, $C_6$-$C_{22}$ alkyl amines, trialkyl-phosphonic acid, trialkyl-phosphine oxides, and trialkyl-phosphines.

The passification can be adjusted by the formulator to provide QN having different properties. For example, provided are two methods for converting hydrophobic nanoparticles to hydrophilic, water soluble nanoparticles. In a first method, the passification layer, for example, tri-n-octylphosphine oxide or hexadecylamine, that coats and protects the outer layer of the final nanoparticle, can be exchanged for a ligand or ligands that are more suitable for the intended use or biological target. One method for exchanging the surface ligands is to dissolve the nanoparticles in a suitable solvent that comprises a large excess of the desired ligand, or simply in a solution of the ligand itself if the ligand is a liquid. For exchanging the hydrophobic ligands typically used to prepare the disclosed nanoparticles, the nanoparticle is dissolved in a suitable solvent in which the new ligand is not soluble and a second solvent containing the desired hydrophilic ligand in a significantly larger quantity is added. The non-miscible liquids are intimately mixed and the nanoparticles will gradually transfer to the second liquid as the ligand exchange occurs. Dialysis or precipitation-redispersion cycles can be used for purification and removing the excess ligands.

A second method for rendering hydrophobic nanoparticles water soluble relates to a process that allows the original passification layer to remain intact. This can be accomplished by adsorption onto the nanoparticle one or more amphiphilic polymers or phospholipids that contain a hydrophobic segment and a hydrophilic segment. Polymers which are suitable for use include polyethylene glycol, alkylamine-modified polyacrylic acid, polyalkyleneoxy-derivatized phospholipids, DL-lactide-co-glycolide-co-polyalkyleneoxy block copolymers, and amphiphilic polyanhydrides. The lipophilic regions of the polymer interact with the lipophilic passification layer thereby extending the hydrophilic region of the polymer outward thereby making the nanoparticle water soluble.

In an embodiment, the passification layer comprises a $C_{12}$-$C_{22}$ carboxylic acid. In an iteration of this embodiment, the layer comprises a carboxylic acid chosen from hexadecanoic acid (palmitic acid), octadecanoic acid (stearic acid), (Z)-$\Delta^9$-octadecenoic acid (oleic acid), (Z,Z)-$\Delta^{9,12}$-octadecadienoic acid (linolenic acid), (Z,Z,Z)-$\Delta^{9,12,15}$-octadecatrienoic acid (linolenic acid). In another iteration, the layer comprises a $C_1$-$C_{25}$ carboxylic acid chosen from octanoic acid, nonanoic acid, decanoic acid, undecanoic acid, dodecanoic acid (lauric acid), tridecanoic acid, tetradecanoic acid (myristic acid), pentadecanoic acid, hexadecanoic acid (palmitic acid), septadecanoic acid, octadecanoic acid (stearic acid), (Z)-$\Delta^9$-octadecenoic acid (oleic acid), (Z,Z)-$\Delta^{9,12}$-octadecadienoic acid (linolenic acid), (Z,Z,Z)-$\Delta^{9,12,15}$-octadecatrienoic acid (linolenic acid).

For example, the QNs comprise an outer coating of oleic acid. This coating can comprise more or less of oleic acid depending upon the amount of oleic acid that is present during the process. The coating can be adjusted by the formulator in order to form a coating compatible with the intended use of the nanoparticles, for example, as an adduct for biological screening such as a cellular probe.

An advantage of the disclosed processes is that the processes can be scaled up to include volumes in excess of laboratory scale, for example, up to volumes of 5,000 mL or more. In the course of scale up, it is within the purview of one having skill in the art to determine reaction parameters/conditions such as, for example, the ratio of reagents, reaction temperatures, and mixing or stirring parameters predicated on the course of quantum nanostructure formation.

In an embodiment, the methods do not use secondary phosphines as ligands for anion sources. In an embodiment, the anion source does not comprise secondary phosphines. Such secondary phosphines can comprise alkyl groups, aryl groups, or a combination thereof. Examples of secondary monophosphine compounds include, bis(3,5-bis(trimethylsilyl)phenyl)phosphine, bis(4-chlorophenyl)phosphine, bis(3,5-di-tert-butylphenyl)phosphine, bis(3,5-ditrifluoromethylphenyl)phosphine, bis(2-furyl)phosphine, bis(4-methylphenyl)phosphine, 1,2-bis(phenylphosphino)ethane, 1,3-bis(phenylphosphino)propane, bis(4-trifluoromethylphenyl)phosphine, bis(3,4,5-trimethoxyphenyl)phosphine, bis(2,4,6-trimethylphenyl)phosphine, dibenzylphosphine, di-n-butylphosphine, di-tert-butylphosphine, dicyclohexylphosphine, diisobutylphosphine, diisopropylphosphine, diphenylphosphine, phobane, di-2-norbornylphosphine, diethylphosphine, dicyclopentylphosphine, dicyclohexylphosphine, di-t-butylphosphine, di-n-propylphosphine, di-1-adamantylphosphine, 1,3-bis(isopropylphosphino)propane, bis(3,5-dimethylphenyl)phosphine, di-n-octylphosphine, di-n-hexylphosphine, di-n-heptylphosphine, di-n-propylphosphine.

In another embodiment, the methods do not use a diphosphine formed from a secondary phosphine as a ligand for an anion source. Examples of such disphosphine compounds include, but are not limited to, tetraphenylbisphosphine.

In an embodiment, the methods do not use secondary phosphine chalcogenide compounds, such as secondary phosphine selenide, secondary phosphine sulfide, and secondary phosphine telluride compounds, formed from the reaction of a secondary phosphines with a chalcogen source (e.g. sulfur, selenium, tellurium, or compounds thereof) as anion sources. Examples of such secondary phosphine chalcogenide compounds include, but are not limited to, secondary phosphine selenide, secondary phosphine sulfide, secondary phosphine telluride, secondary phosphine arsenide, and secondary phosphine antimonide.

In another embodiment, the methods do not use secondary arsine (R(R')AsH) compounds and secondary antimony compounds (R(R')SbH) as anion sources. Examples of these compounds include the As and Sb analogs to the secondary phosphines discussed in the embodiments above.

The methods can provide QNs having a desirable size distribution without the need for any work-up (e.g., washing, precipitation, dialysis, chromatography, and centrifugation) or performing post-preparation procedures to eliminate certain QDs. Accordingly, in an embodiment, the method does not comprise any such work-up or post-preparation procedures.

The steps of the method described in the various embodiments and examples disclosed herein are sufficient to produce the quantum nanostructures of the present disclosure. Thus, in an embodiment, the method consists essentially of a combination of the steps of the methods disclosed herein. In another embodiment, the method consists of such steps.

Compositions

In an aspect the present disclosure provides quantum nanostructures. In an embodiment, the present disclosure provides a composition comprising quantum nanostructures. The quantum nanostructures can be made by the methods disclosed herein. In an embodiment, the quantum nanostructures are made by a method of the present disclosure.

The shape of the quantum nanostructures of the present disclosure can be spherical. The shape of the quantum nanostructures can also be other than spherical, for example, the quantum nanostructures can be "tablet-shaped" similar to a common pill. The quantum nanostructures can also be ovoid, ellipsoid, nonspheriods (e.g. cubes and other box shapes), caged structures as well (e.g. fullerenes) or have an irregular shape.

The QNs can have a narrow size distribution. In an embodiment, a plurality of QDs having a narrow size distribution (e.g., the QNs are substantially monodisperse) is provided without work-up (e.g., washing or centrifugation) or performing post-preparation procedures to eliminate certain QDs. For example, QDs having a size greater than 4 nm can have a dispersity of less than 5%.

In an embodiment, the QNs are substantially monodisperse. The term "substantially monodisperse" when describing QNs denotes a population of nanoparticles of which a major portion, typically at least about 60%, in another aspect from 75% to 90%, fall within a specified particle size range. A population of substantially monodisperse nanoparticles deviates 15% rms (root-mean-square) or less in diameter and typically less than 5% rms. In addition, upon exposure to a primary light source, a substantially monodisperse population of QNs is capable of emitting energy in narrow spectral linewidths, as narrow as 12 nm to 60 nm full width of emissions at half maximum peak height (FWHM), and with a symmetric, nearly Gaussian line shape. The formulator will recognize, the linewidths are dependent on, among other things, the size heterogeneity (i.e., monodispersity) of the QNs in each preparation.

The composition of the QNs can be controlled over a wide range. In an embodiment, the radial composition of the QNs is controlled. For example, a QD having a radial composition can be formed starting with 100% CdSe at the center and a CdSe/Zn gradient from the center to a 100% ZnSe surface can be formed by starting with a nucleation with CdSe seeds and then adding a solution of 90% Cd-oleate and 10% Zn oleate, then change the percentage to 80/20, 70/30, etc. (or even finer changes in relative percentages).

The surface of the QNs can be controlled. A desired surface composition (e.g., surface concentration of anions or cations) can be obtained without the need for post particle formation reactions. For example, the QN can have an anion (e.g., chalcogen) terminated surface, a cation (e.g., Pb or Cd) terminated surface, or a selected combination thereof. For example, the QN can have a surface composition ranging from 90% Cd: 10% S to 10% Cd: 90% S. The QN surface can be from 70% to 100%, including all integer percent values and ranges therebetween, anion terminated or cation terminated. In various embodiments, the QN surface is at least 70%, at least 80%, at least 90%, at least 95%, or at least 99% anion terminated or cation terminated.

By selecting a desired surface for the QN, the QNs can have desirable properties. The photoluminescence efficiency can be controlled. It is expected that the photoluminescence spectrum and/or surface trapping charges (e.g., electron or hole) can be controlled. For example, chalcogen terminated QNs do not exhibit fluorescence and cation terminated QNs exhibit high levels of fluorescence. As another example, the photoluminescence can be modulated by choosing a desired surface composition. This can be used to create a sensor based on modified PL when a cation or anion is bound to the surface (i.e. a sensitive surface for appropriate anions or cations).

Biological Conjugates

In an aspect, the present disclosure provides biological conjugates comprising the QNs. In an embodiment, the biological conjugates comprise QNs and a biological analyte conjugated thereto.

The disclosed nanoparticles are suitable for use in biological assays, as reporters for biological cellular interactions, and as diagnostic tools. For many of the biological applications described herein below, the ligand which is used to prepare the nanoparticle, inter alia, tri-n-octylphosphine oxide that forms the passification layer, must be exchanged or adapted in order to make the nanoparticle water soluble.

The biological analyte conjugated to the QN, can be attached to the hydrophilic end of a polymer or phospholipid that is used to form the water soluble QN. Alternatively, prior to modification of the passification layer, a reactive ligand can be exchanged for a portion of the passification layer and then one end of the reactive ligand can react with the biological analyte to form a linking group. FIG. 16 depicts an enzyme linked by a unit L to a continuously photoluminescent nanoparticle as disclosed herein. As can be seen the tether is connected at the terminus of the peptide chain away from the enzyme's active site so as not to interfere with the activity of the enzyme. The length of the tether can be from 5 to 100 nanometers, depending upon the type of analyte and its function.

FIG. 17 depicts a portion of the passification layer a water soluble continuously photoluminescent nanoparticle wherein the nanoparticle is made water soluble by forming a bi-layer along the surface of the passification layer and wherein the analyte is conjugated to the nanoparticle by association with a surfactant making up the bilayer.

The QNs can be used as diagnostic screens, for example, as diagnostic assays for cancer. Body fluid, inter alia, blood and urine, are analyzed for the presence of biological markers that indicate the presence of cancerous tissue. The concentration of many of these markers is very low, therefore, the sensitivity of present techniques can miss the presence of a cancer related indicator in many instances. For example, prostate cancer is screened for by measuring the level of prostate-specific antigen. However, many other types of cancers are not yet detected by serum assays. Conjugating one of the disclosed nanoparticles to an antigen specific to a particular type of cancer or tumor cell, allows for the detection of malignancy when the abnormal cells are present in very low concentration and therefore leads to an early detection of the disease.

Whether conjugated to the QN by a direct chemical linker or through affinity, for example, the biological analyte is attached to an amphiphilic material that associates with the passification layer, and the QN can be used to track and to monitor the activity of the presence of a biological species.

Methods of Using Nanoparticles

In an aspect, the disclosure relates to methods of using the QNs. Included herein are methods for adapting the properties of the QNs to meet the various needs of the formulator or investigator. Thus, the present disclosure further relates to methods of using the disclosed nanoparticles. One aspect relates to a probe comprising one or more QNs for determining the presence or function of a biological analyte. The biological analyte can comprise one or more of the following amino acids, nucleic acids, saccharides, triglycerides, fatty acids, or organic compounds.

Broadly the methods comprise: a) conjugating a biological analyte with a continuously photoluminescent nanoparticle to form a tagged analyte; b) irradiating the tagged analyte; and c) monitoring the tagged analyte.

The modification of the QNs in a manner suitable to render the nanoparticles useful for the herein described biological applications is described in U.S. Pat. No. 6,326,144 B1, issued to Bawendi et al., Dec. 4, 2001, which is incorporated herein by reference in its entirety. The methods for modifying quantum dots as described in U.S. Pat. No. 6,326,144 B1, can be applied to the instant QNs.

An aspect of the disclosure relates to QNs having an affinity for one or more biological analytes. In an aspect, the nanoparticle is conjugated to a biological analyte in a cell. In another aspect, the nanoparticle is connected to a biological analyte by a linker. In another aspect, the nanoparticle has affinity for a cellular-active compound.

In yet another aspect, the QN has affinity for an organic compound introduced into the cell. In another aspect, the organic compound introduced into the cell is a pharmaceutically active ingredient.

In yet another aspect, the QN has affinity for a cellular-active compound that is formed within a cell. In yet another aspect, the nanoparticle has an affinity for a biological analyte containing amino acids, nucleic acids, saccharides, triglycerides, or fatty acids.

Another aspect of the disclosure relates to a probe for determining the presence or function of a biological analyte. In an aspect, the QN is conjugated to a biological analyte. In another aspect, the nanoparticle is used to probe a biological analyte containing amino acids, nucleic acids, saccharides, triglycerides, fatty acids, or an organic compound that conjugates with the nanoparticle wherein the nanoparticle becomes conjugated to the analyte. In a further aspect the probe is used to track or determine the presence of an analyte in vivo, in vitro, or ex vivo.

As a method for continuously tracking the interaction of a biological analyte and a biological effector in a cell, the method comprises: a) forming a biological analyte/nanoparticle conjugate within a cell, wherein the nanoparticle emits continuous photoluminescence at a first wavelength; b) forming a biological effector/nanoparticle conjugate ex vivo, wherein the nanoparticle emits continuous photoluminescence at a second wavelength; c) introducing the biological effector/nanoparticle conjugate into the cell containing the biological analyte/nanoparticle conjugate; and d) monitoring the photoluminescent emission of the conjugates.

Additional uses of the QNs include thin-film light emitting devices (LEDs), low-threshold lasers, optical amplifier media for telecommunication networks, for relay of encrypted information.

A non-limiting example of a non-biological method that utilizes the disclosed QNs relates to the transmission of encrypted information. For example, a method of sending encrypted information from a sender to a receiver, comprising: a) generating at the sender a series of individual photons from a QN source; b) directing the series of individual photons through a means for polarizing each photon passing in sequence, wherein the amount that each photon is polarized is pre-determined and known by the receiver; and c) directing the series of polarized photons to a receiver capable of determining whether the polarized photons are received in their pre-determined sequence.

The following examples are presented to illustrate the present disclosure. They are not intended to limiting in any manner.

Example 1

Figure 1:
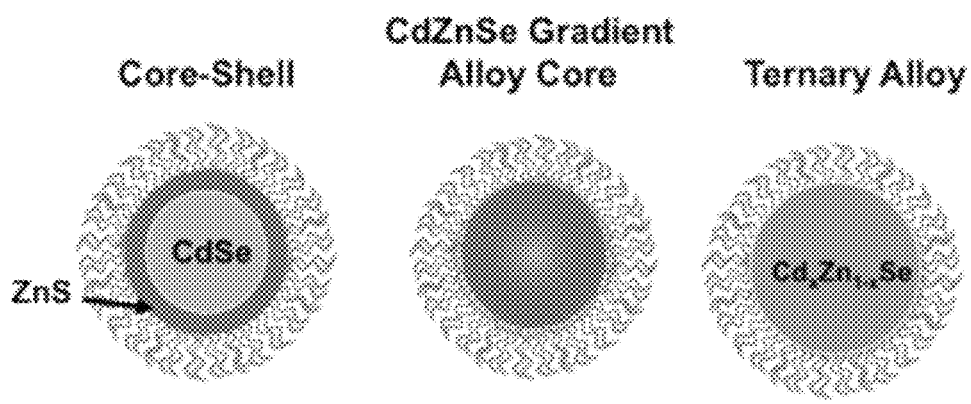
FIG. 1. Graphical representation of a core-shell (left), graded alloy (center), and homogeneous alloy (right) QD structure.

This example describes a new procedure that was discovered to synthesize semiconductor QDs. It was found that it is possible to produce a specific sized nanoparticle by tuning the relative amount of nucleation and growth within the reaction flask. The procedure is based on new understandings of the chemical reaction processes involved in nucleation, such that the relative rates of both nucleation and growth can be controlled based on different chemical precursor molecules with different relative reactivity. Therefore, the number and size of QDs can be tuned by using experimental controls. Specifically, rather than having to quench a reaction at specific times to achieve a given sized QD, this new procedure is designed such that the reaction stops at a given QD size. Thus, there is the potential to synthesize specific sized nanoparticles as desired. This method is reproducible, scalable, and has quantitative higher conversion yields than current methods. Further, it can be applied to synthesize more complicated QD materials such as core-shell structures, alloy structures, and band-gap engineered structures (e.g., FIG. 1). This method results in lower material costs due to vastly reduced labor costs, and thus make the resulting materials economically viable for numerous applications in biomedical imaging, renewable energy, lasers, optoelectronics, and displays.

It was discovered that nucleation of II-VI and IV-VI semiconductor QDs is controlled by disproportionation of the cation ligand sphere to provide the reactive monomer that reacts to form the QDs. The ligand displacement can be best envisioned as an acid-base equilibrium (as shown in FIG. 2—Scheme 1). In other words, the relative ability of an anion-cation chemical precursor pair to make QD monomer is governed by simple rules for acid-base equilibria. Thus, the class of potential QD chemical precursors is large, including any metal-ligand complex that has acidic and/or basic properties. Therefore, the potential precursor sources for the anion and cation include thousands of molecules.

Figure 3:
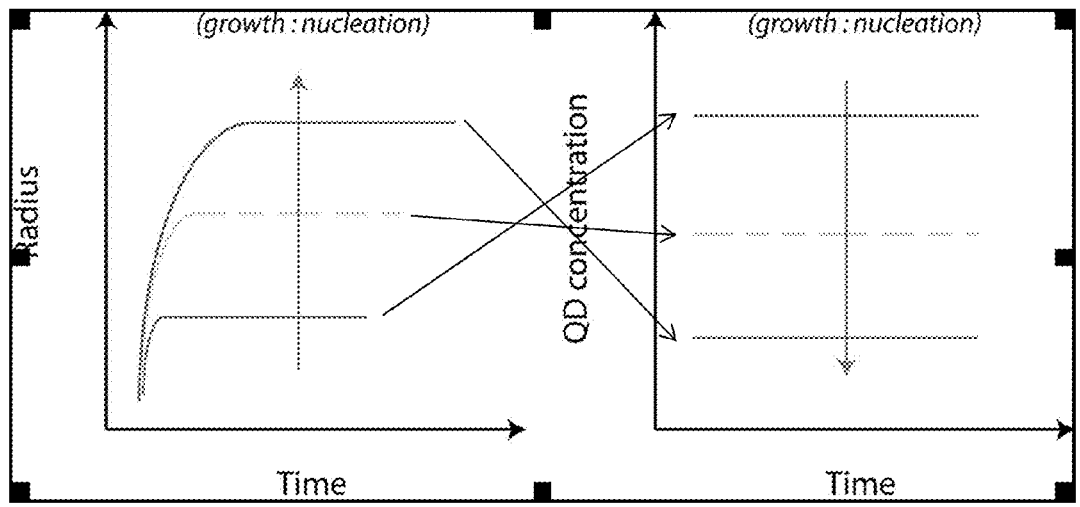
FIG. 3. An example showing that by varying the relative proportion of growth and nucleation within a QD synthesis it will be possible to tune both the size and concentration of the product. For the same amount of Cd and Se precursors, faster reacting ligands generate more QDs that are smaller while slower reacting ligands generate less QDs that grow larger.
Figure 4:
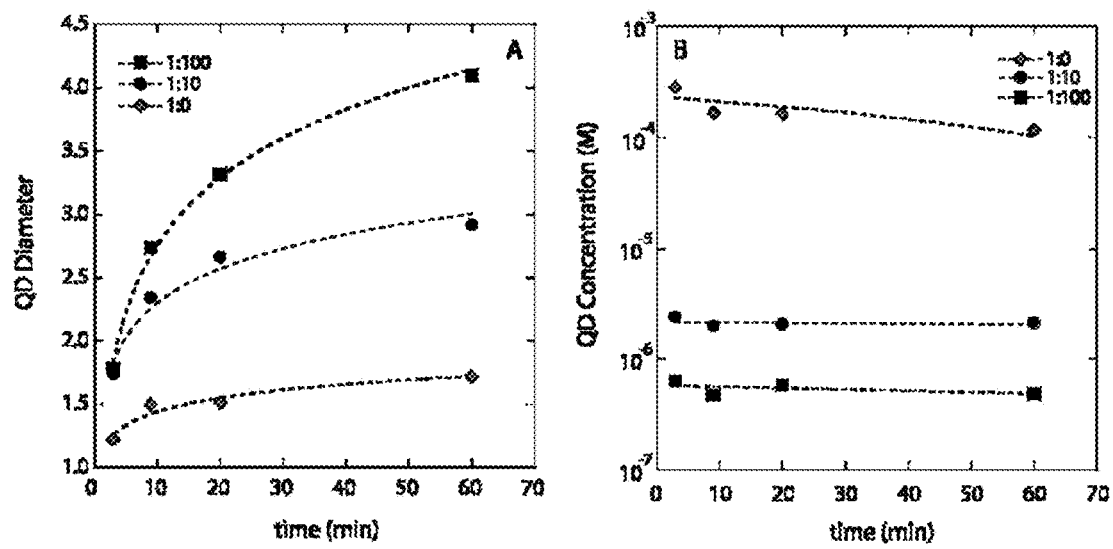
FIG. 4. An example of CdSe QD synthesis undertaken at 160° C. while varying the ratio of Cd-oleate:Cd-octadecylphosphonate and maintaining the same molar quantities of reagents. These results highlight the potential control over QD synthesis when nucleation and growth can be independently varied.

The acid-base tunable ligands were used to exert exact control over the QD size through tuning their relative reactivity. A fast reacting ligand was used to nucleate a lot of monomer and then use a much slower reacting ligand to grow those monomers in size. With respect to synthesis of CdSe QDs, use of a very acidic ligand results in a weakly basic conjugate anion upon disproportionation (FIG. 2—Scheme 1), which will not be easily protonated by the weakly acidic secondary phosphine upon forming the monomer. Such is the case for phosphonic acids; whose $pK_{a1}$ is 2.6, and difficulty making monomer for this case would be expected. By comparison, carboxylic acids (such as acetic, oleic, stearic acids, etc.) have a pKa of 4.7 and should be displaced from metal centers much faster than phosphonic acid metal complexes, making much more monomer in this case. This disparity in reactivity between Cd-carboxylates and Cd-phosphonates can be exploited to direct the growth of specific-sized quantum dots. Utilizing a two-component mixture with both fast and slow acting reagents a synthesis can be tuned to direct both the overall number of particles (nucleation) and their size (growth) (FIG. 3). The concentration of fast reacting cadmium salts (carboxylates) will rapidly decrease and stoiciometrically produce large numbers of nuclei. Upon complete depletion of carboxylate salts the less reactive phosphonate salts will slowly react with DPPSe and generate monomer that can add to the surfaces of the large number of nuclei. Independent nucleation events in the growth phase (i.e. monomer reacting with monomer), which limit the use of fast reacting precursors traditional in the synthesis, should be rare because the concentration of nuclei will always be higher than the concentration of reactive monomer species. Monomer molecules will find an abundance of nuclei surfaces with which to add epitaxially. Growth will cease upon the exhaustion of the slow reagent (phosphonates).

The total number of particles resulting from the QD synthesis will be directly related to the amount of fast reagent. The size of the QD will then be determined exclusively by the ratio of slow to fast reagent (FIG. 3). After combining diphenylphosphine selenide (DPPSe) with excess Cd-oleate, at room temperature, the reaction went to completion immediately and yielded a yellow-colored solution (indicative of extremely small CdSe QDs called magic-sized clusters (MSCs)). However, under identical conditions, no reaction is observed between Cd phosphonic acids and DPPSe. The stronger binding phosphonic acids aren't displaced at room temperature by the acidic phosphine chalcogenide. Rather, 100% conversion was achieved only after heating the reaction mixture to 160° C. for greater than 60 minutes.

In addition to the improvements in size-control; the synthetic scheme detailed above can potentially improve scale-up and decrease the production costs for QDs. The current synthetic methods are performed at 300° C. and require hours of preparation time, possess poor conversion yields, are irreproducible, and lack scalability. This new method can be performed at much lower temperatures (160° C.; see FIG. 3), requires less preparative time, has quantitative conversion yields, and can be scaled to much larger volumes because the kinetics of mixing and nucleating is removed from the growth process. All of these improvements will lead to a dramatic decrease in QD production costs.

Example 2

Example of colloidal semiconductor quantum dots with tunable surface composition.

Colloidal CdS quantum dots (QDs) were synthesized with tunable surface composition. Surface stoichiometry was controlled by applying reactive secondary phosphine sulfide precursors in a layer-by-layer approach. The surface composition was observed to greatly affect photoluminescence properties. Band edge emission was quenched in sulfur terminated CdS QDs and fully recovered when QDs were cadmium terminated. Calculations suggest that electronic states arising from surface sulfur atoms could trap holes and thus inhibit radiative recombination.

Described is the synthesis of CdS QDs using secondary phosphine sulfide (DPP-S) and Cd-stearate in tetradecane. By taking advantage of the highly reactive DPP-S precursor, high-quality CdS QDs were synthesized with controllable size (2.8 to 5.2 nm in diameter), a narrow size distribution (±11%), and under a relatively low nucleation temperature (160° C.), which is significantly lower than most conventional CdS QD syntheses. Importantly, the complete conversion of S in DPP-S to CdS allowed for unprecedented control over the CdS QD surface composition using a SILAR (successive ionic layer adsorption and reaction) type process. CdS QD surface composition could be tuned from essentially all Cd to all S termination as confirmed by X-ray photoelectron spectroscopy (XPS). The chemical composition of the surface was observed to have a dramatic effect on the band edge photoluminescence (PL) of the QDs. Terminating the CdS QD core with sulfur completely quenched PL emission while capping with cadmium restored the full magnitude of the PL intensity. Additionally, it was found that the PL intensity scaled directly with the relative percentage of Cd or S atoms on the surface. It is expected that the use of highly reactive QD chemical precursors coupled with an understanding of chemical reaction mechanism should allow for the design of novel QDs with controllable optical properties.

Synthesis of cadmium sulfide QDs was based on previously reported hot injection synthesis methods and carried out using DPP-S and Cd stearate in tetradecane under a positive pressure of nitrogen at 160° C. The nucleation temperature was lower than typical CdS QD syntheses (typical syntheses operate at >200° C.) due to the high reactivity of DPP-S precursor. To make larger QDs with controllable surface composition, first a CdS QD core was synthesized approximately 2.8 nm in diameter. Next, SILAR was applied to grow the CdS QD core larger. Specifically, DPP-S in tetradecane was injected into the QD solution, and the rapid and complete consumption of the DPP-S resulted in a S-rich shell nominally one monolayer thick on the QD surface. Subsequently, Cd-stearate was then injected forming a monolayer Cd-rich shell. This process was repeated several times to grow the CdS QD to a desired size.

Figure 5:
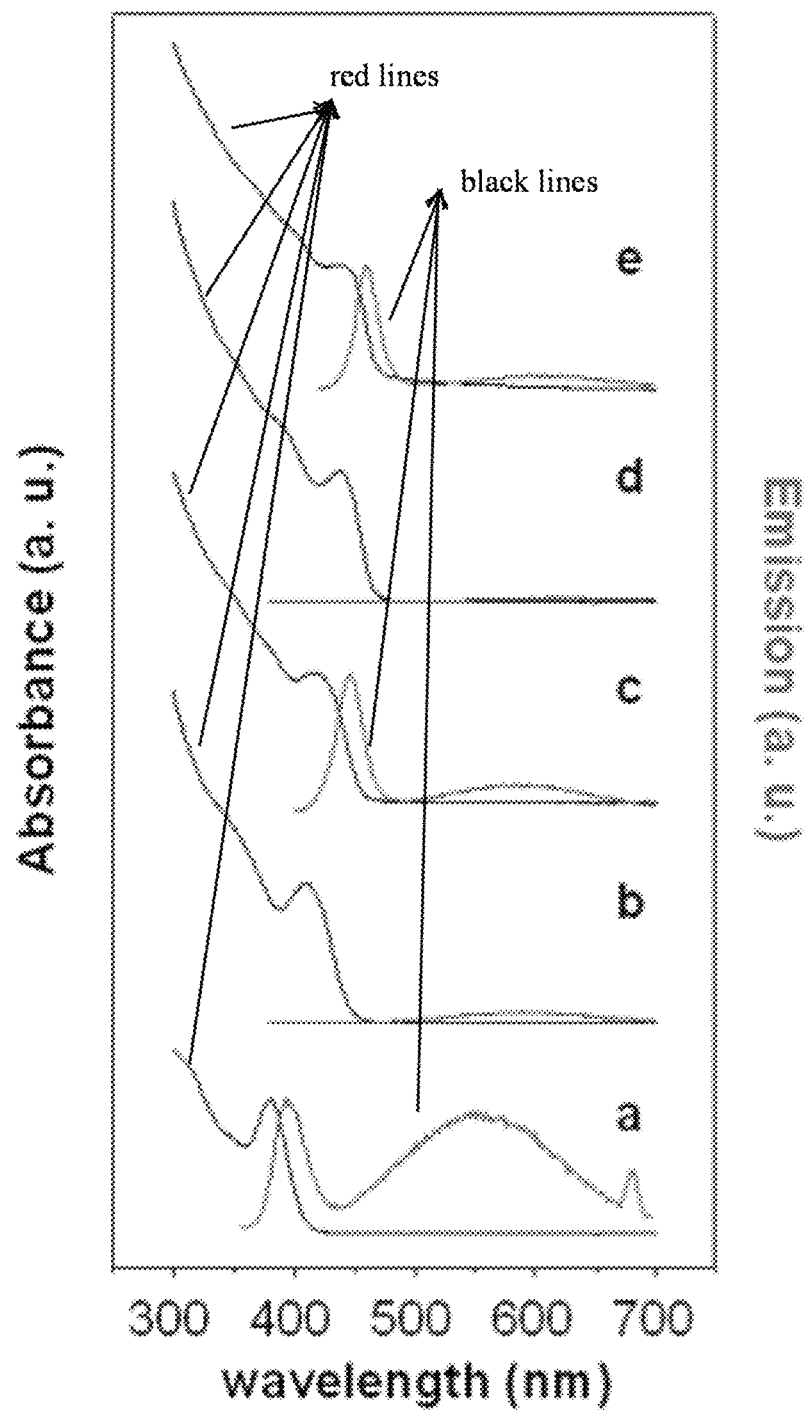
FIG. 5. Examples of absorption (black line) and photoluminescence (PL) spectra (red line) of (a) as prepared CdS QDs, (b) QDs from (a) after addition of one monolayer of DPP-S, (c) QDs from (b) after addition of one monolayer of Cd stearate, (d) and (e) absorption and PL spectra after an additional monolayer of S (d) or Cd (e) was added. The small sharp peak around 680 nm in (a) is due to an overtone of the excitation wavelength. The narrow peak close to the absorption peak is band edge photoluminescence while the broad band around 550 nm is due to surface state emission and is common for CdS QDs of this size.
Figure 8:
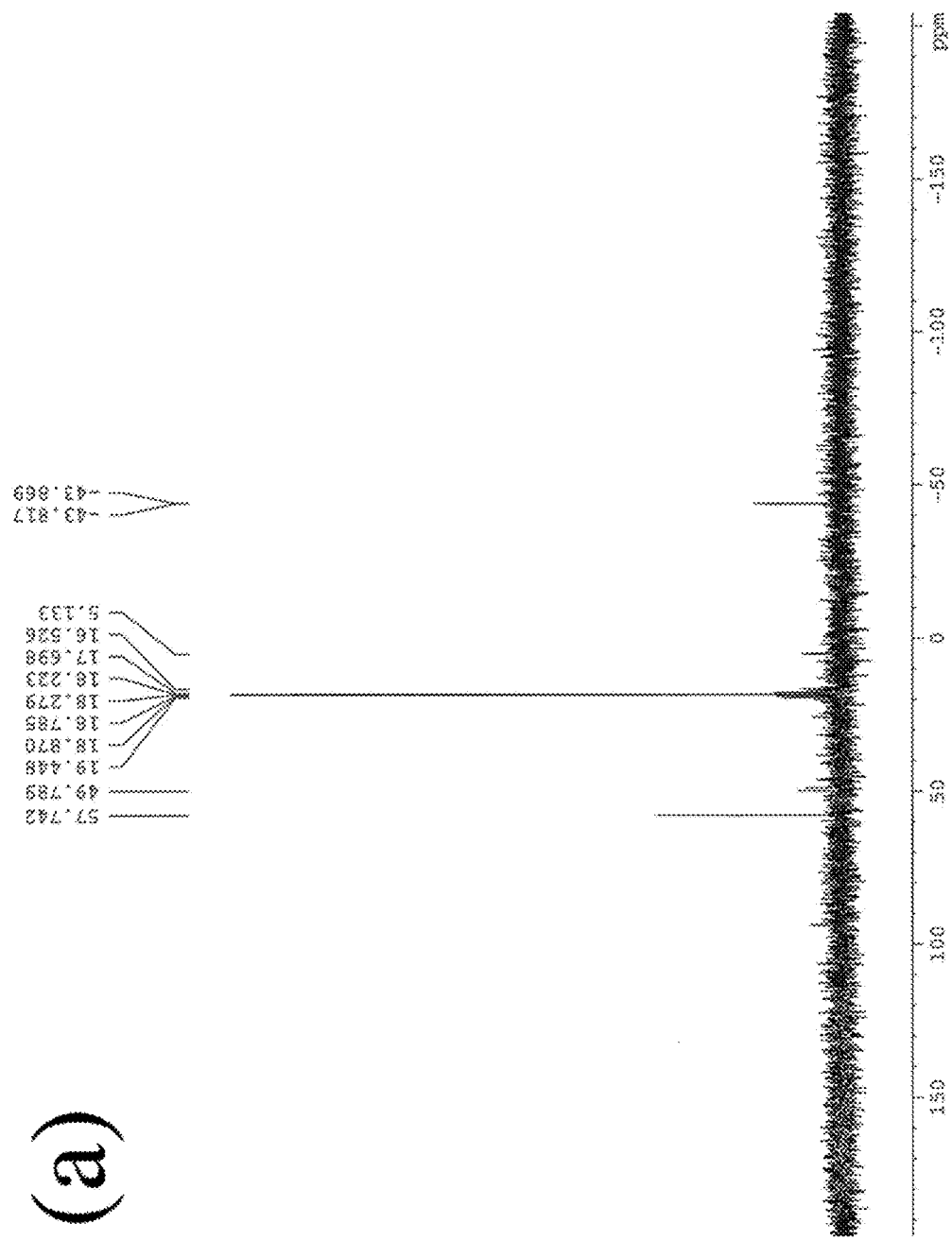
FIG. 8. Example of NMR raw data showing diphenylphosphine sulfide (DPP-S) (a) before and (b) after addition of Cd-oleate at 170° C. for 8 minutes. The solvent was octadecene (ODE). The peaks at −43.8 ppm and 18.2 ppm correspond to DPP and DPP-S, respectively. (Note that DPP was added in slight excess to ensure complete conversion of all elemental S to DPP-S). The peak near 57.7 ppm in (a) corresponds to a 5% impurity compound containing P and S that forms under the reaction conditions used to make DPP-S. Note that after reaction with Cd-oleate, the DPP-S has completely reacted with Cd to form CdS nanoparticles, leaving predominantly DPP in the spectrum.
Figure 8:
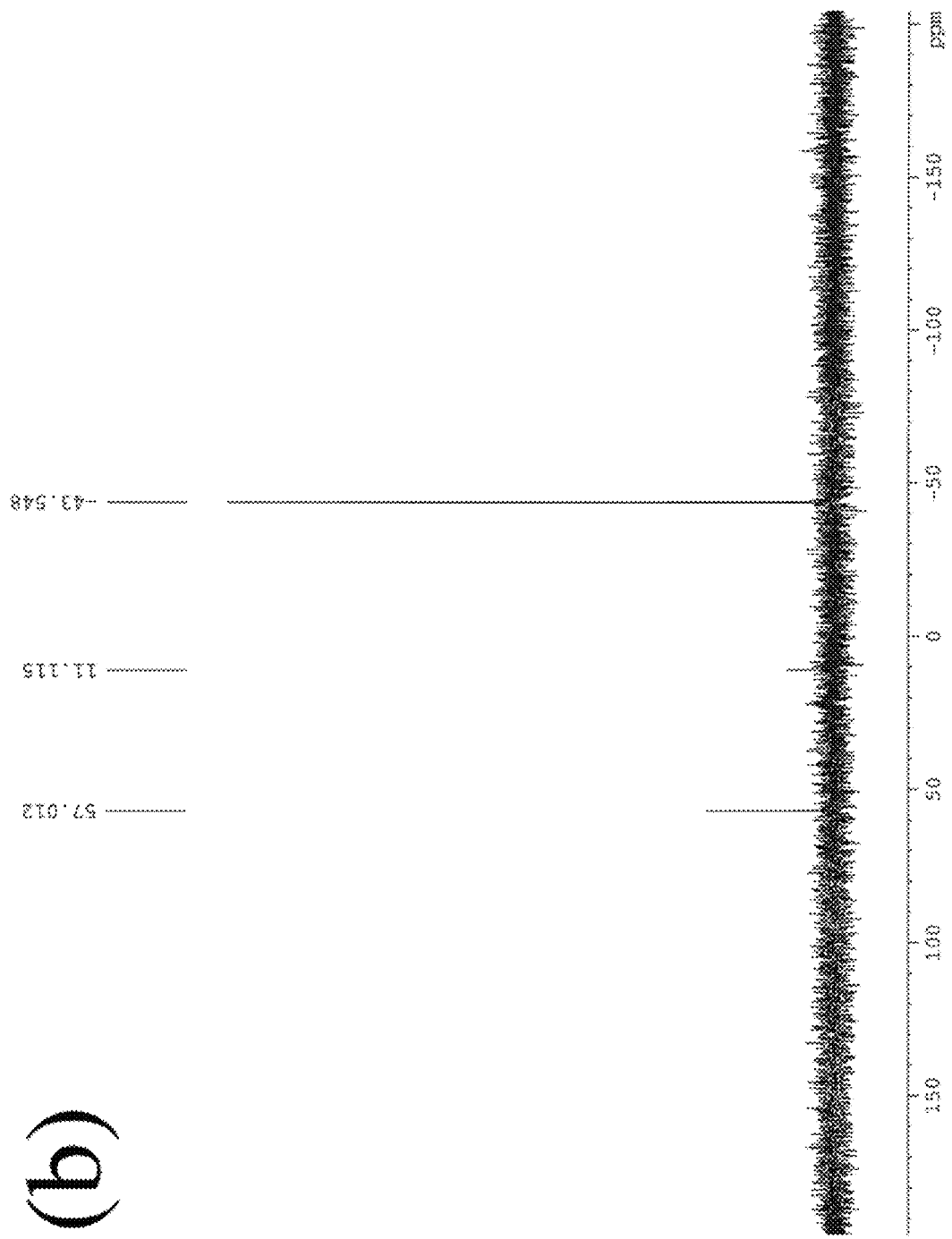

FIG. 5 illustrates the absorption and fluorescence properties of a series CdS QDs with increasing size (and varied surface composition) as subsequent monolayers of cadmium and sulfur are added to the QD. The gradual red shift of the first exciton absorption peak from 381 nm in FIG. 5a to 447 nm in FIG. 5e indicates the size of QDs continually increased after repeated monolayer addition. Thus, after each SILAR injection procedure it was concluded that the added precursor reacted with the surface of the CdS QD core. Due to the high reactivity of secondary phosphine selenides, it was assumed that all injected Cd or S reacted to completion with the QD surface, as from NMR data it is clear that all DPP-S was consumed after addition of Cd-oleate (FIG. 8). As the QDs grew larger the full-width half-maximum (FWHM) of the first excitonic absorption feature decreased slightly (275 to 250 meV) while the FWHM of the PL spectrum remained relatively constant at ~170 meV, indicating good control over the QD size as additional monolayers are added.

The PL intensity of the CdS QDs exhibited significant changes as subsequent layers of Cd or S were added to the QD surface. Band edge PL emission was surprisingly and completely quenched when CdS QDs were capped primarily with DPP-S (FIG. 5b). Even more surprising was that the band-edge PL intensity and spectrum completely recovered upon terminating the QD with primarily Cd-stearate (FIG. 5c). Also noteworthy was that capping the as produced cores with Cd diminished the contribution from surface trap emission (FIG. 9); surface trap emission is commonly observed in small CdS QDs due to their higher surface-to-volume ratio. In addition, the whole process could be repeated, as quenched and recovered PL was observed in CdS QD emission spectra as alternative S and Cd terminated surfaces were added (FIGS. 5d and 5e, respectively).

Figure 6:
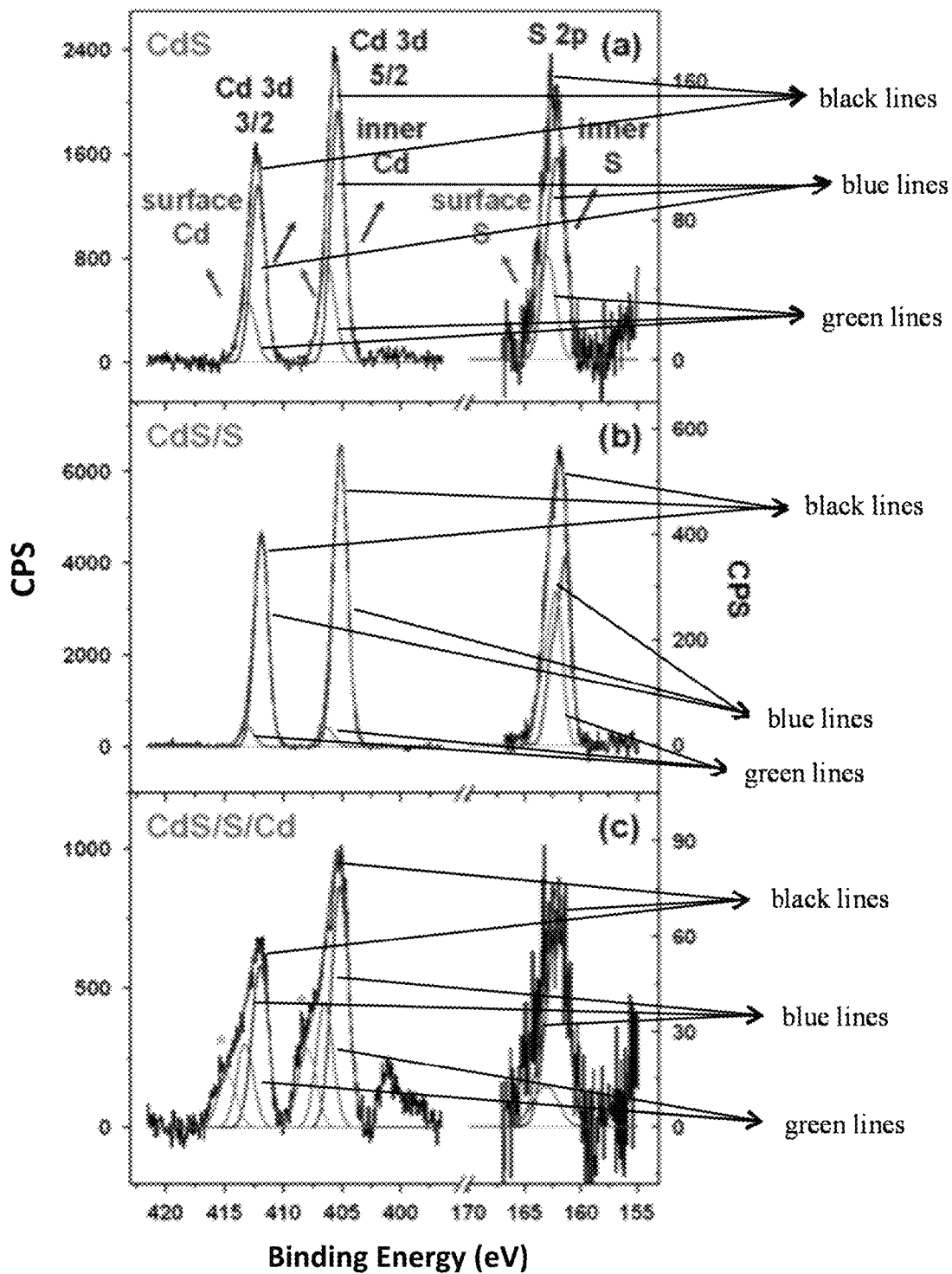
FIG. 6. Example of XPS elemental analysis on three CdS QDs: (top row) (a) CdS-A, (middle row) (b) CdS-B, and (bottom row) (c) CdS-C. Left column corresponds to XPS counts from Cd 3d electrons and the right column is XPS data from S 2p electrons. Black lines represent raw XPS data; blue lines are Gaussian curve fits at energies corresponding to core atoms while green lines are Gaussian curve fits centered at energies corresponding to electrons from atoms on the surface. S signals included contributions from S 2p 1/2 and 3/2 electrons. Detail fitting of S 2p 1/2 and 3/2 peaks are described in Example 2. Asterisks in (c) indicate oxidized Cd peaks which blue-shifted from inner and surface Cd signals both in Cd 3d 3/2 and 3d 5/2.
Figure 7:
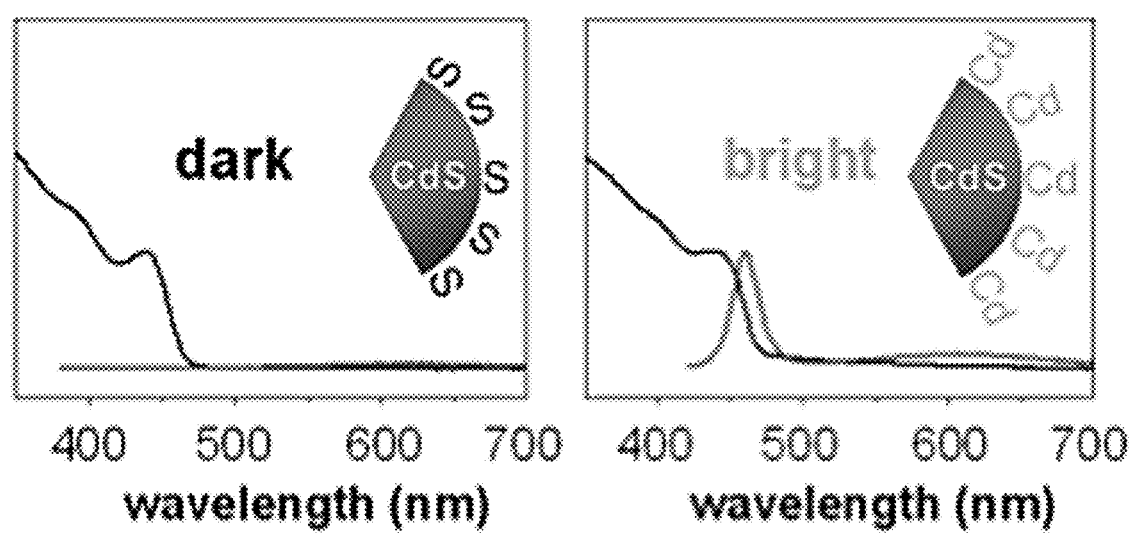
FIG. 7. Example of emission and PL spectra for sulfur surface terminated QDs (left) and cadmium surface terminated QDs (right).

Surface composition of CdS QDs was determined by X-ray photoelectron spectroscopy (FIG. 6). XPS is a well-known and reliable technique used to distinguish surface from sub-surface atoms in solid state materials. In this case XPS can provide an accurate determination of elemental composition of CdS QDs due to the distinct core electron binding energies of cadmium and sulfur: cadmium 3d 5/2 and 3/2 electrons have their binding energies at 405 and 412 eV, respectively, while the binding energies for sulfur 2p 3/2 and 1/2 electrons are 162 and 163 eV. For CdS QDs, the ratio of number of atoms of Cd to S can be determined from the integrated Cd and S signals, which are themselves corrected by an appropriate atomic sensitivity factor (S) provided in the instrument. It has been previously shown that surface atoms have binding energies slightly blue-shifted from bulk values. Thus, the ratio of the number of surface to inner atoms of cadmium (and likewise sulfur) can be determined from the XPS Cd (or S) data by taking a ratio of the integrated XPS peaks for the surface and core atoms, respectively.

Three CdS QD samples were prepared for XPS analysis: (1) small CdS QD cores, denoted CdS-A, (2) S-terminated CdS (CdS/S) denoted as CdS-B corresponding to a single DPP-S addition to CdS-A and (3) Cd-terminated CdS (CdS/S/Cd) denoted as CdS-C corresponding to a single Cd-sterate addition to CdS-B. To determine the relative percent of Cd to S on the surface, first the overall number of Cd and S atoms in the QD were determined by using the integrated XPS data for each atom and assuming a spherical QD with a radius determined from the wavelength of the first absorption peak. Next, the relative fraction of surface-to-inner atoms of Cd or S was determined from the ratio of the integrated areas for the surface or core atom curve fits to the raw XPS data. Finally, by combining the total number of atoms (of either Cd or S), with the percent of surface atoms, the relative percentage of Cd or S on the surface can be determined. The fitting peaks for the S signals in each sample shown in FIG. 6 include surface S (or inner) atoms from two S 2p signals (1/2 and 3/2). Details of S signal fitting and the calculation of the surface atom chemical composition and associated fitting parameters for each sample are described in this example. Note also that a third fitting peak was added to model the Cd signals in CdS-C (marked with asterisk) and attributed to oxidized Cd on the surface which is 2.8 eV shifted from inner Cd signal and 1.5 eV shifted from surface Cd signal.

Figures 9, 10:
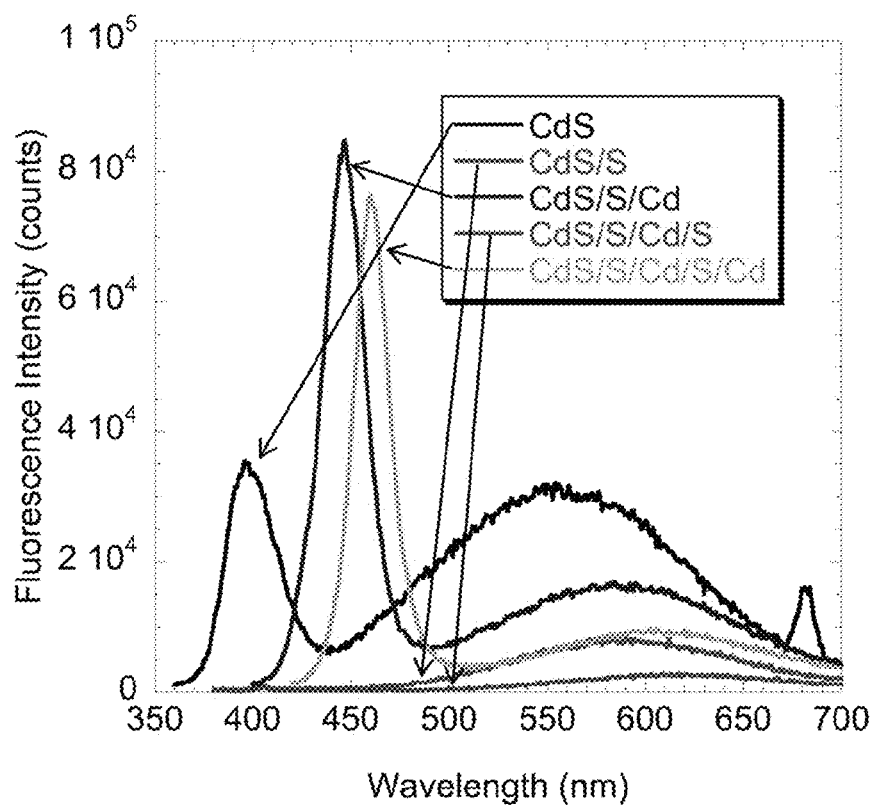
FIG. 9. Example of raw photoluminescence spectra for as prepared CdS nanocrystals and CdS nanocrystals with one monolayer of sulfur added, a subsequent additional layer of Cd added, a second additional layer of sulfur added and finally a second additional layer of Cd added. Spectra were acquired for the same relative absorbance such that relative efficiencies of photoluminescence can be compared. Note that as additional Cd or S layers are added the relative contribution of the surface state emission (broad peak in the range of 550 to 650 nm) decreases.
FIG. 10. Table 1—Example of XPS elemental analysis of three CdS batches A, B and C. Table shows the atomic percentage of elements in each sample obtained from raw XPS data. D is the diameter of the QDs modeled from $1^{st}$ extinction peak of its absorption spectrum. Surface-to-inner ratio of Cd and S ($Cd_s/Cd_i$ and $S_s/S_i$) are calculated from integrated peak area fitted from Cd and S signals in XPS data.
Figure 11:
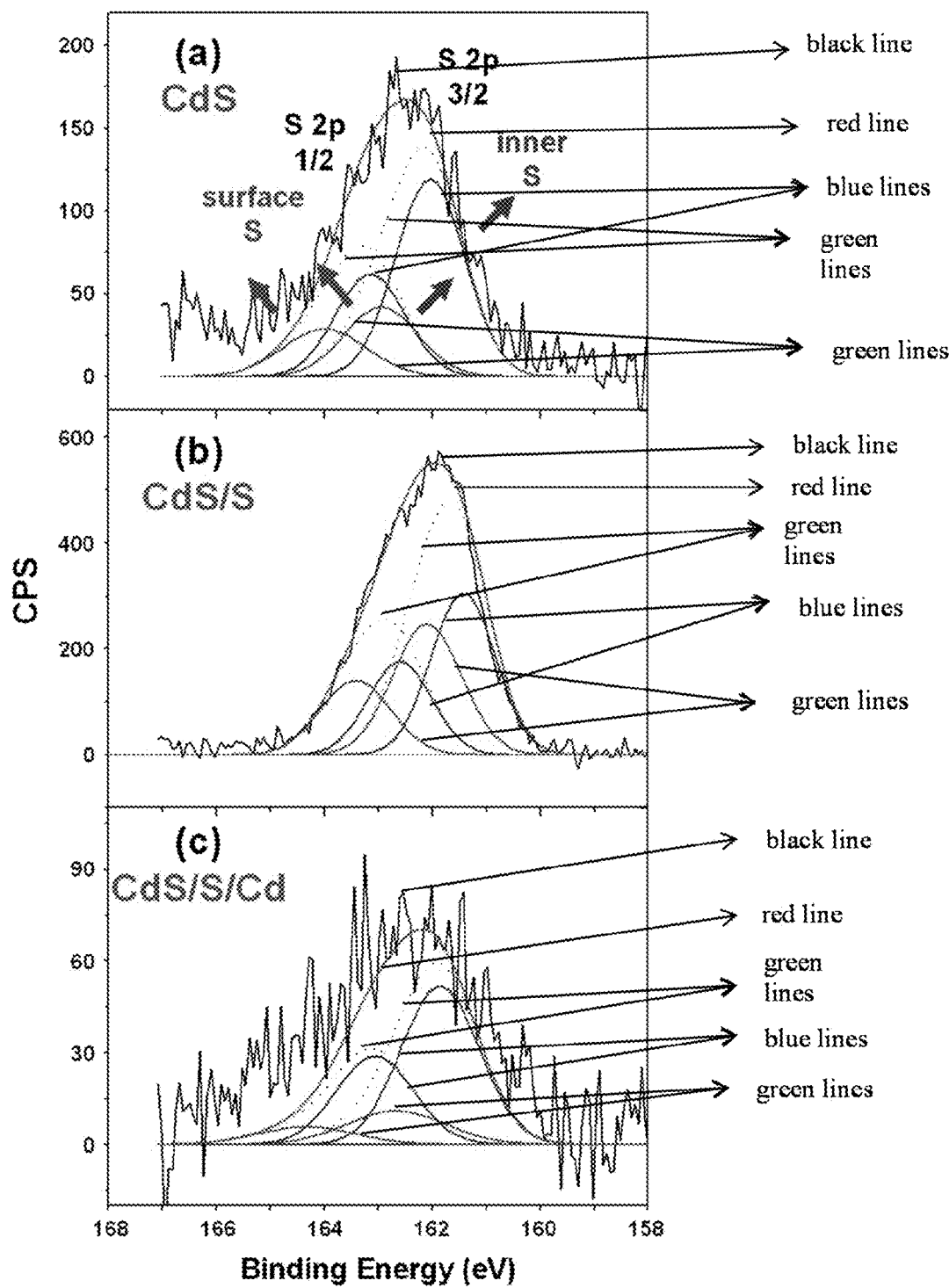
FIG. 11. Example of XPS raw data and Gaussian fitting peaks of S signals in three CdS samples: as prepared (a) CdS, (b) CdS/S and (c) CdS/S/Cd. Fitted peaks for S 2p 1/2 (~163 eV) and S 2p 3/2 (~162 eV) are individually shown in each spectrum, represented by dotted lines. Blue lines (fitted peaks) indicate signals from inner sulfur atoms while green lines represent signals from surface atoms.

The calculated percentages of Cd and S atoms on the QD surface for each sample are presented in FIG. 10—Table 1. The ratio of the number of surface-to-inner atoms for Cd in CdS-A was calculated to be 0.45; while for S this value was 0.50. After accounting for the relative numbers of Cd and S atoms in the interior of the QD, it was found the surface composition to be almost half Cd and half S for the CdS-A sample. Note that very small QDs, such as the CdS-A sample, have a non-stoichiometric ratio of Cd to S atoms in the core (CdS-A was Cd-rich), which must be accounted for in the analysis of the chemical nature of the surface atoms. For the CdS-B sample, the number of surface-to-inner atoms for Cd was 0.08, while for S this value was 0.84. As expected, this sample with the additional monolayer of S added had an extremely S-rich surface, consisting of 13% Cd and 87% S. Finally, the CdS-C sample, which had an additional monolayer of Cd added, had essentially a Cd terminated surface, calculated at 91% Cd and 9% S (surface-to-inner ratio of Cd and S as 0.94 and 0.12, respectively).

TABLE 3

List of XPS composition analysis of three CdS QDs batches: CdS-A (as prepared CdS), CdS-B (S-terminated CdS) and CdS-C (Cd-terminated CdS). Diameters of QDs were calculated from first extinction peak in absorption spectra from each sample individually, overall Cd-to-S ratio were obtained from XPS.

|  | D (nm) | Cd/S ratio | Cd/S corrected | $Cd_s/Cd_i$ ratio | $S_s/S_i$ ratio | Surface % Cd | S |
|---|---|---|---|---|---|---|---|
| CdS-A | 2.84 | 1.42 | 1.36 | 0.45 | 0.50 | 56 | 44 |
| CdS-B | 3.96 | 0.94 | 0.92 | 0.08 | 0.84 | 13 | 87 |
| CdS-C | 4.26 | 2.44 | 2.38 | 0.94 | 0.12 | 91 | 9 |

Figure 14:
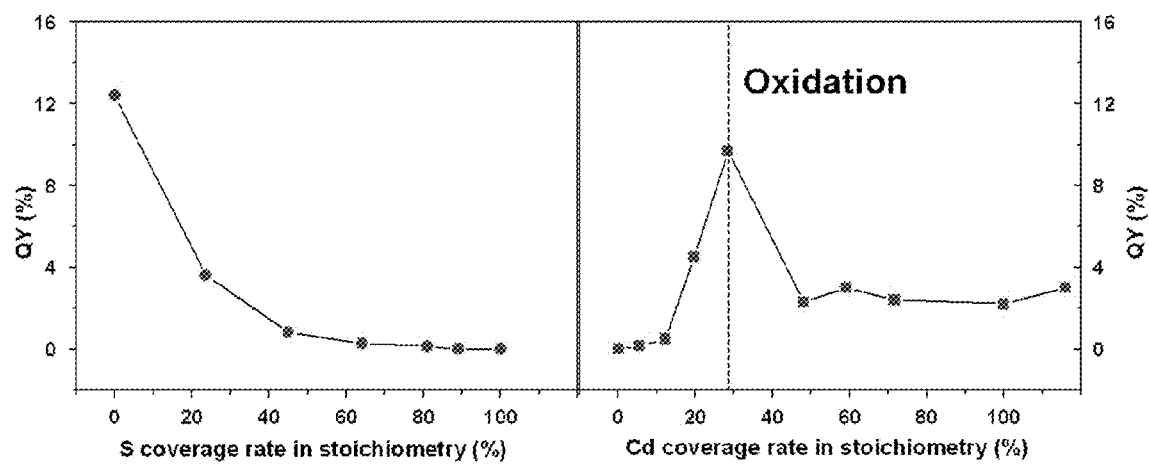
FIG. 14. Example of a plot of PL QY versus surface coverage for incremental monolayer addition. Left plot shows the QY decreases as DPP-S was successively added to Cd-terminated CdS QDs while the right plot shows how the QY changes in a reverse experiment: Cd-stearate was gradually added to S-terminated CdS QDs. The QY increased when Cd-stearate was added and reached its maximum (QY ~10%)

Supporting the idea that the relative amount of surface Cd or S determined the PL intensity, measurements of the PL intensity with the surface composition varying between all Cd and all S were performed. Not surprisingly, it was found the CdS QD band edge PL intensity varied directly with the amount of added DPP-S precursor (to a QD with a Cd terminated surface). When the amount of surface S was increased through successive injections of DPP-S, the PL intensity decreased proportional to the surface coverage of DPP-S (see FIG. 14). Addition of Cd precursor caused the PL intensity to recover. However, the PL intensity reached its maximum when Cd coverage was calculated to be only about 20%, which was attributed to oxidation of the QD surface due to the numerous precursor injections (through a rubber septum). Note that full recovery of PL intensity was consistently observed when a full amount of Cd precursor for one monolayer of Cd was added at once, minimizing the chance for additional oxygen to enter the reaction vessel.

The quenching of PL intensity for CdS QDs with an S-terminated surface could potentially be attributed to several factors. For example, capping semiconductor QDs with thiols (such as through a ligand exchange with phosphine or acidic aliphatic ligands) is known to quench PL through a process attributed to the introduction of hole traps. It was thus hypothesized that the termination of the CdS QDs with a sulfur shell would likewise introduce surface trap states that provide for effective non-radiative recombination pathways.

To test this hypothesis, calculations of the density of Cd and S energy states were performed on representative CdS QDs with either a stoichiometric surface, or QDs that were terminated with predominantly Cd or S (FIG. 18). The ideal $Cd_{33}S_{33}$ cluster was initially constructed using density functional theory (DFT—details in experimental section) possessing a wurtzite lattice with bulk Cd—S bond lengths and then relaxed to its lowest energy configuration. Once the ideal QD was fully relaxed, 1, 3, or 5 Cd (S) atoms were replaced with S (Cd) atoms to simulate a Cd (S)-rich QD. These modified structures were then each relaxed to their lowest energy state.

When larger Cd atoms were used to replace smaller S atoms, the size of the QD slightly increased, and the energy gap narrowed, due to both decreased quantum confinement and appearance of defect states near the edges of the valence and conduction bands. However, a well-defined energy gap remained, with no evidence of mid-gap surface trap states. On the other hand, with an increasingly S-rich surface numerous mid-gap surface states began to appear in the densities of electronic states (DOS). Such mid-gap states provide efficient non-radiative recombination pathways for electrons or holes, as evidenced by the time-domain ab initio simulations. Thus, it was concluded that for S-rich QDs, efficient non-radiative recombination mediated by the mid-gap surface states quenches fluorescence, in agreement with the experimental data (FIGS. 5b,d).

The origin of the mid-gap states in the sulfur-rich QDs becomes apparent from the analysis of the bonding patterns in the non-stoichiometric clusters, FIG. 18. Sulfur atoms tend to form few covalent S—S bonds, creating noticeable flaws (i.e. dangling bonds) in the geometry of the QD surface. On the other hand, Cd atoms are capable of producing continuous structures even in highly nonstoichiometric clusters due to the metallic nature of Cd—Cd bonding. Changing the surface composition introduces stoichiometric defects that promote self-healing through structural reorganization. Gap states are determined by the electronic properties of the cluster in the region of nonstoichiometric make-up, and the energetics of the gap states depend on the elemental composition of the surface.

With such a dramatic change in the band structure for both the Cd and S-rich systems, it is somewhat surprising that the absorption spectra remain relatively unchanged as Cd or S monolayers are added, FIG. 5. This observation can be rationalized by an analysis of the localization of the states near the band gap. The data shown in FIG. 15 indicates that mid-gap surface states have highly localized electron densities, while the states of the valence and conduction bands are delocalized over the whole QD. The localized nature of the mid-gap states is important for two reasons. First, it limits the overlap of the wave-functions of free charge carriers in the valence and conduction bands with the wave-functions of the charges trapped in the surface states. As a result, gap states exhibit low optical activity and are not seen in the absorption spectra of larger QDs. Second, the localized nature of the surface states supports the hypothesis that trapped surface charges can pull subsequent electron/hole pairs apart causing a reduction in radiative decay.

To verify that the mid-gap states created in the S and Cd-rich systems were in fact optically inactive, time-dependent (TD) DFT calculations were performed with the PBE exchange and correlation functionals and the LANL2dz basis set in the Gaussian 09 code. The calculated absorption spectra can be seen in FIG. 20. Note that the red-shift of the TDDFT spectra relative to the experimental data (refer to FIG. 5) is a known drawback of pure DFT functionals, such as PBE, while hybrid functionals showing better agreement with experiment are computationally more expensive. Nonetheless, the trend in absorption with QD stoichiometry is very clear. As expected, mid-gap states (i.e. absorption features at ~900 nm, and 1200 nm) have an absorbance almost an order of magnitude less than the main band-edge absorption peak. Note that in order to keep the computation times reasonable the calculated absorption spectrum corresponds to QDs a factor of 2 to 4 smaller in diameter than the measured QDs. Since the surface-to-volume ratio decreases rapidly with increasing QD diameter, the overlap, and therefore the optical coupling between surface and core states drops proportionally as well. Thus, the ratio of the intensities of the mid-gap states and the main QD core excitonic peaks shown in FIG. 20 will rapidly decrease in larger QDs, in agreement with the experimental data, FIG. 5.

While trapping of holes at sulfur surface atoms may significantly reduce or quench PL intensity, other explanations were also considered. For example, charge transfer of electrons or holes to the surface ligands could considerably inhibit radiative recombination. Interfacial charge separation and transfer between QDs and adsorbates has been reported in several cases: methyl viologen ($MV^{2+}$) and $TiO_2$ were found to be electron quenchers, a Ru-polypyridine complex acted as hole quencher and rhodamine B (RhB) can quench electrons or holes.

In addition to the unexpected photophysics in the CdS QDs, a surprisingly strong effect of the solvent on the resulting CdS QDs synthesized using secondary phosphine precursors (FIG. 19) was noticed. In particular, the physical properties of CdS QDs were compared when synthesized in saturated and unsaturated solvents, tetradecane and 1-octadecene (ODE) respectively. As seen in FIG. 19a, the absorption spectrum for QDs synthesized in ODE seems to display poorly resolved excitonic states, indicating a broader size distribution, although the linewidth of the PL spectra is similar for the two cases. However, for the ODE solvent TEM microscopy confirmed nanoparticles with highly irregular sizes and shapes, including high-aspect ratio rod-like particles (FIG. 19c). By contrast, TEM images for QDs synthesized in tetradecane show QDs that are almost spherical and uniform in size. The origin of the long tail in the absorption spectrum of the QDs synthesized in tetradecane is unclear, as from TEM the QDs appear fairly uniform in size and shape. It is proposed that the long tail is due to absorption from weakly active surface states, which also exhibit weak PL as seen in FIG. 19a.

It is proposed that the stark difference in the nanoparticle product for tetradecane versus ODE synthesis is due to the presence of the olefin on ODE. During the QD synthesis reaction, it was postulated that it is possible for the secondary phosphine to add across the double bond in ODE. For example, hydrophosphination of diphenylphosphine was reported in alkene and alkyne reactant with transition metal catalysts that lead to the formation of tertiary phosphines. Formation of tertiary phosphine sulfides is expected to considerably slow reaction rates. The dynamic mixtures of secondary and tertiary phosphines would effectively lead to a constantly changing reaction rate for the formation of QDs and thus non-spherical shapes can be expected. By contrast, use of the non-coordinating solvent tetradecane provides no opportunity for the secondary phosphine to react with the solvent. Further, the ligand of the cadmium salt precursor was changed to stearic acid from oleic acid to be consistent with a purely saturated solvent. Thus, well-controlled QD size and shape are expected in this case.

The synthesis of CdS QDs using secondary phosphine sulfide (DPP-S) and Cd-stearate in tetradecane was demonstrated. CdS QDs synthesized via DPP-S and Cd-stearate were produced with diameters ranging from 2.5 to 5.5 nm with the important quality that their surface composition can be precisely controlled. It was found that surface composition of CdS QDs had a significant effect on the photoluminescence of QDs. Band-edge PL was completely quenched in DPP-S terminated CdS QDs, but completely recovered in Cd-stearate terminated QDs. Calculations on Cd and S rich QDs suggest that localized surface states mediate fast non-radiative recombination and thus are responsible for the PL quenching behavior. More generally, synthesis of semiconductor QDs with the highly reactive secondary phosphines provides an opportunity to control optical properties of QDs by precisely manipulating the desired surface composition of the nanoparticles during their formation.

Experimental. Chemicals.

Cadmium oxide (CdO, Aldrich, 99.99%), Sulfur powder, Diphenylphosphine (DPP), stearic acid (SA), acetonitrile, toluene and tetradecane were purchased and used without any further purification.

DPP-S Synthesis.

DPP-Se synthesis procedures in our previous report were followed and revised to make DPP-S. 20 mmol S (0.6414 g) and 20 mmol DPP (3.48 mL) were well mixed in 25 mL toluene under an inert gas for 20 minutes leading to a transparent colorless solution. The solvent was removed and white wax-like raw product was obtained. Needle-like DPP-S crystals were re-crystallized with acetonitrile and toluene in a refrigerator. DPP-S crystals were dried and stored in a glove box with an inert atmosphere. DPP-S (0.6 mmol, 0.13 g) was dissolved in 6 mL tetradecane to make a 0.1 M DPP-S solution.

Cd-Stearate Synthesis.

CdO (1.25 mmol, 0.16 g) was mixed and heated with stearic acid (10 mmol, 2.845 g) in 9 mL tetradecane at 160° C. for 1 hour until the solution color changed from brick-red to colorless. The temperature was raised to 240° C. for a few minutes to make 0.1 M Cd-stearate solution. Cd-stearate is a solid at room temperature, so heat must be applied prior to use. Cd-sterate was stored in the glove box.

CdS Synthesis.

The synthesis procedure was adapted from a previously reported hot injection method. QD synthesis was performed on a Schlenk line under an inert gas. 2.6 mL tetradecane, 0.895 g stearic acid and 600 µL 0.1 M Cd-stearate were loaded into a sealed flask. Freeze-pump-thaw cycles were performed to remove oxygen and then inert gas was added and the flask was heated to 160° C. 400 µL of 0.1 M DPP-S solution was rapidly injected at 160° C. immediately yielding QDs which were allowed to grow for 20 min.

SILAR on CdS Core.

Precursor amounts for each additional layer were calculated based on size and surface area of the quantum dot. As prepared CdS QDs were kept in a sealed flask under inert gas and then the calculated amount of DPP-S dissolved in tetradecane for one monolayer was injected at 160° C. and reacted for 10 min to produce S-terminated CdS (CdS/S). In the same flask and at the same temperature, Cd-stearate was injected to form Cd-terminated CdS (CdS/S/Cd) after 40 min of growth. Fractions of CdS QDs in each stages of continuous SILAR were withdrawn and precipitated out by centrifuging in excess acetonitrile to remove organic ligands and unreactive species for further characterizations.

Optical Characterization.

Absorption spectra were taken on a Perkin-Elmer Lambda 950 UV/Vis/NIR spectrophotometer and PL measurements were taken on an Acton fluorometer system. Samples were dissolved in toluene and placed in a 1 cm square cuvette. Optical densities of fluorescence samples were controlled to be 0.1.

X-Ray Photoelectron Spectroscopy Spectra and Analysis.

XPS data were taken with Al $K_\alpha$ as the source of incident X-rays. Samples were washed with acetonitrile to remove all ligands, precursors and solvent for several times and then re-dissolved into toluene. Thick CdS QD films were drop cast on an Au film for XPS measurements. Raw XPS data showed the overall relative number of Cd to S atoms and the atomic sensitivity factor, S, was self-corrected in the default of instrument software, Casa. XPS data were then individually fitted with Gaussian functions to determine the relative signals from the surface and inner atoms. Fitting parameters and details of calculation are shown in the supporting information.

Calculation Details.

The geometry optimization was performed using plane-wave density functional theory (DFT) as implemented in the VASP code. The Perdew-Burke-Ernzerhof (PBE) functional was used in order to describe the electron exchange and correlation interactions. All valence-shell electrons were treated explicitly, while the core electrons were modeled with the projector-augmented-wave pseudopotentials. The simulation was carried out in a cubic cell periodically replicated in three dimensions, as stipulated by the plane-wave basis. To prevent spurious interactions between periodic images of the QD, the cell was constructed to have at least 8 Angstroms of vacuum between the QD replicas.

Sensitivity Calibration.

A calibration procedure described in the literature was followed to correct the overall Cd/S ratio in the XPS measurement taking consideration of varied inelastic mean free path of the photoelectrons escaped from different atoms. In homogeneous materials, the intensity of XPS signals from a single element is:

$$I = nf\sigma\theta y\lambda AT,$$

where n is the number of atoms per cm$^3$, f is the X-ray flux, s is the cross section for photoelectric processes, q is an angular factor, y is the efficiency for formation of a photoelectron with the full kinetic energy, 1 is the area probed and T is a factor for the efficiency of detecting electrons of a given kinetic energy. An overall atomic sensitivity factor, S can be determined.

$$n = 1/(f\sigma\theta y\lambda AT) = 1/S$$

Usually, S would be corrected in the instrument software, and thus would provide the raw Cd/S ratios in the three CdS QDs samples. However, this ratio needs to be further calibrated for QDs because of differences in the electron mean free path of Cd and S.

$$(Cd/S)_{corrected} = \frac{\lambda_{Cd}}{\int_0^d e^{-\frac{z}{\lambda_{Cd}}} dz} \frac{\int_0^d e^{-\frac{z}{\lambda_S}} dz}{\lambda_S} (Cd/S),$$

where d is the depth of material, and the mean free path (1) of Cd and S was calculated to be 16.4 Å for Cd 3d core and 18.2 Å for S 2p core for Al Kα radiation. The correction factors are calculated to be 0.960, 0.974 and 0.976 for the three CdS samples, CdS-A to CdS-C, respectively. The corrected Cd/S ratios of three CdS QDs samples are shown in FIG. 10—Table 1.

Surface Composition Calculation.

A spherical model with a wurtzite crystal lattice was proposed to determine the volume of a CdS quantum dot, where the volume (V) should be:

$$V_{dot} = \frac{4\pi}{3}(r^3),$$

where r is the radius of the dot calculated from its 1$^{st}$ extinction peak in the absorption spectrum. The number of Cd and S atoms in a CdS QD was calculated by dividing the QD volume by the unit cell volume of the wurtzite crystal:

$$N_{Cd} + N_S = 2Z\left(\frac{V_{dot}}{V_{unit\ cell}}\right),$$

where $V_{unit\ cell}$ is the volume of unit cell of CdS in wurtzite (0.09991 nm$^3$). Z=2 means there are 2 pairs of CdS (2 Cd and 2 S atoms) in one CdS unit cell. The overall numbers of Cd and S atoms are determined by the Cd/S ratio (A) acquired from the XPS measurement:

$$N_{Cd} = (N_{Cd} + N_S)\left(\frac{A}{A+1}\right),\ N_S = (N_{Cd} + N_S)\left(\frac{1}{A+1}\right).$$

Assuming x Cd atoms and y S atoms on the surface of the QD, the surface composition (Cd % and S %) of a CdS QD can be calculated as:

$$\frac{x}{N_{Cd} - x} = \frac{Cd_{surface}}{Cd_{inner}},\ \frac{y}{N_S - y} = \frac{S_{surface}}{S_{inner}}$$

where $$Cd\ \% = \frac{x}{x+y},\ S\ \% = \frac{y}{x+y}.$$

Figure 13:
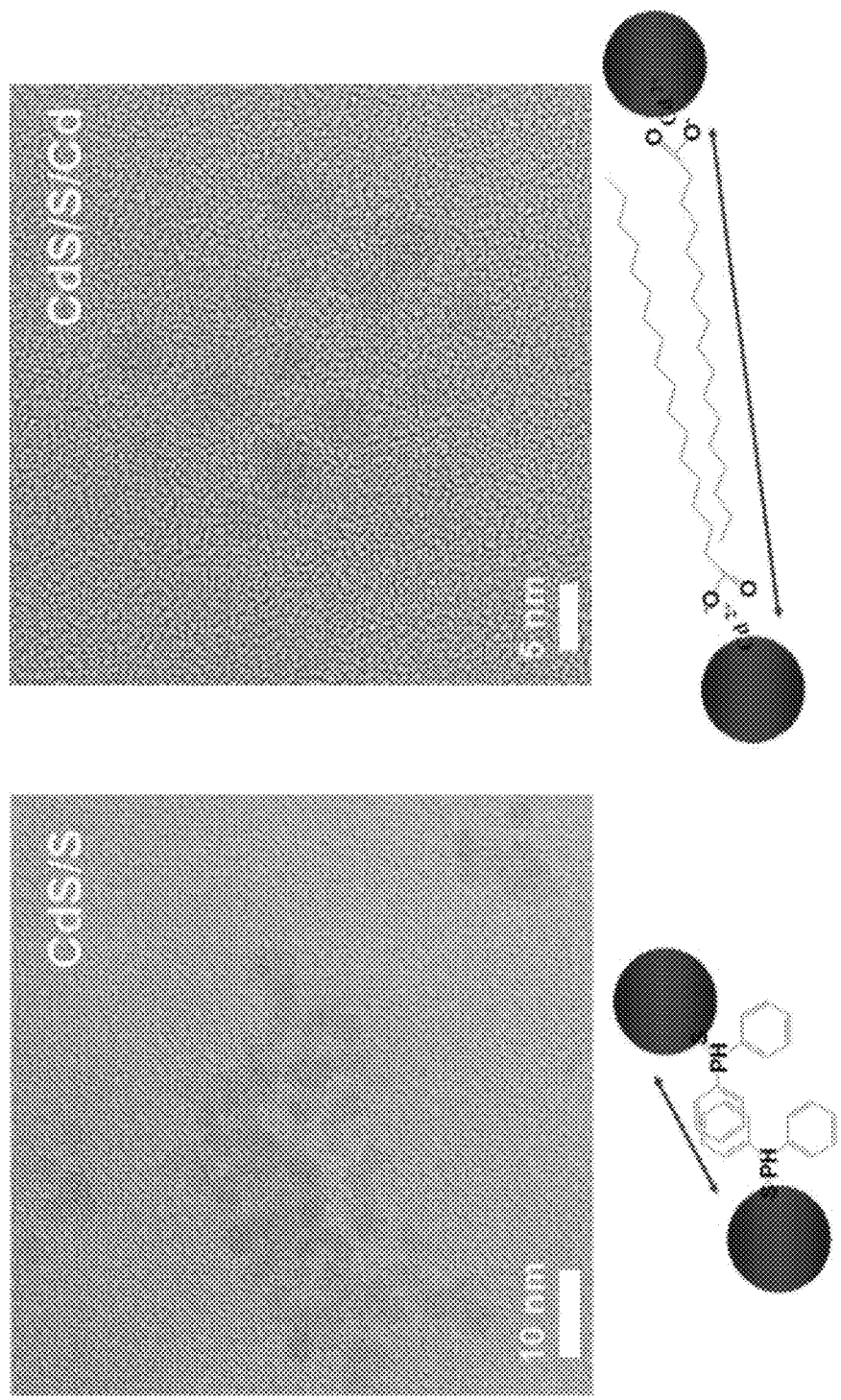
FIG. 13. Exemplary TEM images of two CdS QDs with different surface composition: CdS QDs terminated with sulfur (left) and cadmium (right). It is observed that S-terminated CdS QDs have a smaller inter-particle spacing than Cd-terminated CdS QDs, which may be attributed to the surface ligands. Diphenyphosphine surface composition may lead to close packed QDs particles due to the π-π interactions of the phenyl groups while the long alkyl chain on the oleate group from Cd-terminated QDs should provide a larger spacing between particles. XPS data show small phosphorus signals for S-terminated QDs but not in Cd-terminated CdS QDs suggesting that the diphenylphosphine remains on the surfaces for S-capped QDs.

Further information on the states whose densities are depicted in FIG. 13 is provided in FIG. 18. In particular, parts (a), (b) and (c) of FIG. 13 correspond to the top panel and parts (a) and (d) of FIG. 18, respectively. The HOMO and LUMO of the stoichiometric QD appear at energies of 0 and 1.6 eV. The HOMO and LUMO of the Cd-rich $Cd_{34}S_{32}$ are at 0 and 1.3 eV. The band gap decreases partly due to decreased quantum confinement, since Cd is larger than S, and partly due to appearance of surface defect states near the band edges. The gap state of $Cd_{32}S_{34}$ appears at 0 eV. It is an occupied state, and therefore, it is a hole trap. The gap state is in the middle of the band gap, formed by the HOMO and LUMO orbitals at −0.6 and 1.1 eV.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A process for preparing quantum nanostructures comprising the steps of:
   (a) contacting a first cation source and a second cation source, the first cation source comprising a metal and at least one first ligand and the second cation source comprising the metal and at least one second ligand, and an anion source comprising a metal and at least one ligand, optionally, in a solvent, to form a reaction mixture; and
   (b) maintaining the reaction mixture from (a) at a temperature and time sufficient to form the quantum nanostructures,
   wherein the first cation source is a nucleation source and the second cation source is a growth source, and at least 90% of the first cation source reacts before more than 10% of the second cation source reacts.

2. The process of claim 1, further comprising the step of contacting the first cation source, second cation source, and anion source with one or more additional cation sources and/or one or more additional anion sources to form the reaction mixture.

3. The process of claim 1, further comprising the step of isolating the quantum nanostructures from step (b).

4. The process of claim 1, wherein the first cation source is a carboxylate salt and the second cation source is a phosphonate salt.

5. The process of claim 4, wherein the carboxylate salt is a cadmium carboxylate salt and the phosphonate salt is a cadmium phosphonate salt.

6. The process of claim 1, wherein step (b) is carried out a temperature of from −40° C. to 380° C.

7. The process of claim 6, wherein step (b) is carried out a temperature of from 200° C. to 250° C.

8. A process for preparing quantum nanostructures comprising the steps of:
   (a) contacting a first cation source comprising a metal and at least one first ligand, wherein the first cation source is a nucleation source, and an anion source comprising a metal and at least one ligand, optionally, in a solvent, to form a reaction mixture;
   (b) maintaining the reaction mixture from (a) at a temperature and time sufficient to form quantum nanostructure nucleates and such that quantum nanostructure nucleate size stabilizes;
   (c) adding a second cation source comprising the metal and at least one second ligand to the reaction mixture from (b), wherein the second source is a growth source; and
   (d) maintaining the reaction mixture from (c) at a temperature and time sufficient to form the quantum nanostructures.

9. The process of claim 8, further comprising the step of contacting the first cation source, second cation source, and anion source with one or more additional cation sources and/or one or more additional anion sources to form the reaction mixture.

10. The process of claim 8, further comprising the step of isolating the quantum nanostructures from step (d).

11. The process of claim 8, wherein the first cation source is a carboxylate salt and the second cation source is a phosphonate salt.

12. The process of claim 11, wherein the carboxylate salt is a cadmium carboxylate salt and the phosphonate salt is a cadmium phosphonate salt.

13. The process of claim 8, wherein step (b) and/or step (d) is carried out a temperature of from −40° C. to 380° C.

14. The process of claim 13, wherein step (b) is carried out a temperature of from 200° C. to 250° C.

15. A composition comprising a plurality of quantum nanostructures made by the method of claim 1 comprising quantum nanostructures having a surface terminated by at least 70% cations or anions.

* * * * *

UNITED STATES PATENT AND TRADEMARK OFFICE
CERTIFICATE OF CORRECTION

PATENT NO. : 8,920,766 B2  
APPLICATION NO. : 13/972485  
DATED : December 30, 2014  
INVENTOR(S) : Krauss Page 1 of 1

It is certified that error appears in the above-identified patent and that said Letters Patent is hereby corrected as shown below:

In the claims:

Column 28, line 4, in claim 6, "carried out a" should read:

--carried out at a--;

Column 28, line 6, in claim 7, "carried out a" should read:

--carried out at a--;

Column 28, lines 33-34, in claim 11, "phoshonate" should read:

--phosphonate--;

Column 28, line 39, in claim 13, "carried out a" should read:

--carried out at a--; and

Column 28, lines 40-41, in claim 14, "carried out a" should read:

--carried out at a--.

Signed and Sealed this  
Twenty-ninth Day of March, 2016

Michelle K. Lee  
*Director of the United States Patent and Trademark Office*